(12) United States Patent
Tancredi et al.

(10) Patent No.: US 8,133,476 B2
(45) Date of Patent: Mar. 13, 2012

(54) CALCIUM PHOSPHATE COMPLEX AND SALTS IN ORAL DELIVERY SYSTEMS

(75) Inventors: Doris Tancredi, Sparta, NJ (US); Samantha Holme, Pompton Plains, NJ (US); Shiuh Luo, Livingston, NJ (US)

(73) Assignee: Cadbury Adams USA LLC, Parsippany, NJ (US)

( * ) Notice: Subject to any disclaimer, the term of this patent is extended or adjusted under 35 U.S.C. 154(b) by 291 days.

(21) Appl. No.: 11/732,940

(22) Filed: Apr. 5, 2007

(65) Prior Publication Data

US 2007/0237725 A1 Oct. 11, 2007

Related U.S. Application Data

(60) Provisional application No. 60/789,525, filed on Apr. 5, 2006, provisional application No. 60/789,528, filed on Apr. 5, 2006.

(51) Int. Cl.
*A61K 9/68* (2006.01)

(52) U.S. Cl. .............................. 424/48; 424/50

(58) Field of Classification Search .............. 424/48, 424/50
See application file for complete search history.

(56) References Cited

U.S. PATENT DOCUMENTS

| | | |
|---|---|---|
| 325,711 A | 9/1885 | Stuckes, Jr. |
| 810,210 A | 1/1906 | Laws |
| 943,945 A | 12/1909 | Liebich |
| 1,771,506 A | 7/1930 | Mustin |
| 1,771,982 A | 7/1930 | Mustin |
| 2,004,957 A | 6/1935 | Messner |
| 2,197,719 A | 8/1940 | Conner |
| 2,448,786 A | 9/1948 | Faxon |
| 2,973,273 A | 2/1961 | Curtiss |
| 3,052,552 A | 9/1962 | Koerner et al. |
| 3,071,476 A | 1/1963 | Werft et al. |
| 3,795,748 A | 3/1974 | Cillario |
| 3,806,290 A | 4/1974 | Graff et al. |
| 3,857,963 A | 12/1974 | Graff et al. |
| 3,872,021 A | 3/1975 | McKnight |
| 3,894,154 A | 7/1975 | Graff et al. |
| 3,912,817 A | 10/1975 | Sapsowitz |
| 4,148,872 A | 4/1979 | Wagenknecht et al. |
| 4,150,112 A | 4/1979 | Wagenknecht et al. |

(Continued)

FOREIGN PATENT DOCUMENTS

CA 2589270 A1 5/2007

(Continued)

OTHER PUBLICATIONS

J Dent Res 76 (9): 1587-1595, 1997. Remineralization of Enamel Subsurface Lesions by Casein Phosphopeptide-stabilized Calcium phosphate complex.*

(Continued)

*Primary Examiner* — Gollamudi Kishore
*Assistant Examiner* — Snigdha Maewall
(74) *Attorney, Agent, or Firm* — Hoffmann & Baron LLP

(57) ABSTRACT

The present invention relates to oral delivery systems, such as confectionery and chewing gum compositions, and methods for remineralizing tooth enamel in mammals. In particular, the oral delivery systems include a phosphopeptide or phosphoprotein stabilized calcium phosphate or calcium fluoride phosphate complex and a salt selected from calcium salts, phosphate salts and combinations thereof. The delivery systems promote remineralization of tooth enamel of consumers.

4 Claims, 2 Drawing Sheets

— not significantly different, * significantly different (p < 0.001) to all other values.

U.S. PATENT DOCUMENTS

| | | | |
|---|---|---|---|
| 4,150,161 A | 4/1979 | Rudolph et al. | |
| 4,156,715 A | 5/1979 | Wagenknecht et al. | |
| 4,156,716 A | 5/1979 | Wagenknecht et al. | |
| 4,156,740 A | 5/1979 | Glass et al. | |
| 4,157,385 A | 6/1979 | Wagenknecht et al. | |
| 4,157,402 A | 6/1979 | Ogawa et al. | |
| 4,159,315 A | 6/1979 | Wagenknecht et al. | |
| 4,160,054 A | 7/1979 | Wagenknecht et al. | |
| 4,160,820 A | 7/1979 | Wagenknecht et al. | |
| 4,208,431 A | 6/1980 | Friello et al. | |
| 4,217,368 A | 8/1980 | Witzel et al. | |
| 4,224,345 A | 9/1980 | Tezuka et al. | |
| 4,250,196 A | 2/1981 | Friello | |
| 4,251,201 A | 2/1981 | Krysiak | |
| 4,252,829 A | 2/1981 | Terrevazzi | |
| 4,269,860 A | 5/1981 | Ogawa et al. | |
| 4,271,197 A | 6/1981 | Hopkins et al. | |
| 4,271,198 A | 6/1981 | Cherukuri et al. | |
| 4,271,199 A | 6/1981 | Cherukuri et al. | |
| 4,291,045 A | 9/1981 | Mackay et al. | |
| 4,292,329 A | 9/1981 | Ogawa et al. | |
| 4,301,178 A | 11/1981 | Witzel et al. | |
| 4,316,915 A | 2/1982 | Friello et al. | |
| 4,317,838 A | 3/1982 | Cherukuri et al. | |
| 4,328,249 A | 5/1982 | Mackay et al. | |
| 4,329,369 A | 5/1982 | Tezuka et al. | |
| 4,352,822 A | 10/1982 | Cherukuri et al. | |
| 4,352,823 A | 10/1982 | Cherukuri et al. | |
| 4,352,824 A | 10/1982 | Puglia et al. | |
| 4,352,825 A | 10/1982 | Cherukuri et al. | |
| 4,374,858 A | 2/1983 | Glass et al. | |
| 4,382,962 A | 5/1983 | Devos et al. | |
| 4,399,154 A | 8/1983 | Puglia et al. | |
| 4,421,773 A | 12/1983 | Akutagawa | |
| 4,430,351 A | 2/1984 | Cillario | |
| 4,466,983 A | 8/1984 | Cifrese et al. | |
| 4,485,118 A | 11/1984 | Carroll et al. | |
| 4,513,012 A | 4/1985 | Carroll et al. | |
| 4,543,769 A | 10/1985 | Schmitz | |
| 4,563,345 A | 1/1986 | Arrick | |
| 4,585,649 A | 4/1986 | Lynch | |
| 4,601,907 A | 7/1986 | Knebl et al. | |
| 4,614,654 A | 9/1986 | Ream et al. | |
| 4,614,658 A | 9/1986 | Wilson et al. | |
| 4,642,235 A | 2/1987 | Reed et al. | |
| 4,647,450 A | 3/1987 | Peters et al. | |
| 4,656,039 A | 4/1987 | Weiss et al. | |
| 4,683,138 A | 7/1987 | Glass et al. | |
| 4,707,363 A | 11/1987 | Sato et al. | |
| 4,738,854 A | 4/1988 | Friello et al. | |
| 4,741,905 A | 5/1988 | Huzinec | |
| 4,753,790 A | 6/1988 | Silva et al. | |
| 4,753,806 A | 6/1988 | Carroll et al. | |
| 4,762,719 A | 8/1988 | Forester | |
| 4,828,845 A | 5/1989 | Zamudio-Tena et al. | |
| 4,872,884 A | 10/1989 | Cherukuri et al. | |
| 4,938,128 A | 7/1990 | Knebl | |
| 4,949,630 A | 8/1990 | Knebl | |
| 4,952,407 A | 8/1990 | Record et al. | |
| 4,971,806 A | 11/1990 | Cherukuri et al. | |
| 4,975,288 A | 12/1990 | Hager et al. | |
| 4,980,178 A | 12/1990 | Cherukuri et al. | |
| 4,981,698 A | 1/1991 | Cherukuri et al. | |
| 4,997,659 A | 3/1991 | Yatka et al. | |
| 5,017,385 A | 5/1991 | Wienecke | |
| 5,045,326 A | 9/1991 | Glass et al. | |
| 5,073,389 A | 12/1991 | Wienecke | |
| 5,116,626 A | 5/1992 | Synosky et al. | |
| 5,125,819 A | 6/1992 | Hager et al. | |
| 5,130,123 A | 7/1992 | Reynolds et al. | |
| 5,139,797 A | 8/1992 | Huzinec et al. | |
| 5,156,866 A | 10/1992 | Sato et al. | |
| 5,227,154 A * | 7/1993 | Reynolds | 424/49 |
| 5,244,887 A | 9/1993 | Straub | |
| 5,256,402 A | 10/1993 | Prencipe et al. | |
| 5,279,842 A | 1/1994 | Escola Gallart et al. | |
| 5,344,659 A | 9/1994 | Kurihara et al. | |
| 5,380,530 A | 1/1995 | Hill | |
| 5,399,365 A | 3/1995 | Yatka et al. | |
| 5,425,961 A | 6/1995 | Yatka et al. | |
| 5,431,929 A | 7/1995 | Yatka et al. | |
| 5,458,892 A | 10/1995 | Yatka et al. | |
| 5,498,429 A | 3/1996 | Orlandi et al. | |
| 5,502,045 A | 3/1996 | Miettinen et al. | |
| 5,525,360 A | 6/1996 | Yatka et al. | |
| 5,612,070 A | 3/1997 | Yatka et al. | |
| 5,626,892 A | 5/1997 | Kehoe et al. | |
| 5,626,896 A | 5/1997 | Moore et al. | |
| 5,629,035 A | 5/1997 | Miskewitz | |
| 5,637,334 A | 6/1997 | Yatka et al. | |
| 5,645,821 A | 7/1997 | Libin | |
| 5,670,163 A | 9/1997 | Cuca et al. | |
| 5,672,367 A | 9/1997 | Grijpma et al. | |
| 5,698,215 A | 12/1997 | Kalili et al. | |
| 5,713,738 A | 2/1998 | Yarborough | |
| 5,736,175 A | 4/1998 | Cea et al. | |
| 5,756,074 A | 5/1998 | Ascione et al. | |
| 5,824,291 A | 10/1998 | Howard | |
| 5,833,954 A * | 11/1998 | Chow et al. | 424/49 |
| 5,879,728 A | 3/1999 | Graff et al. | |
| 5,952,019 A | 9/1999 | Yatka et al. | |
| 5,955,116 A | 9/1999 | Kehoe et al. | |
| 6,054,144 A | 4/2000 | Burruano et al. | |
| 6,087,353 A | 7/2000 | Stewart et al. | |
| 6,242,019 B1 | 6/2001 | Bell et al. | |
| 6,264,999 B1 | 7/2001 | Yatka et al. | |
| 6,280,762 B1 | 8/2001 | Bealin-Kelly et al. | |
| 6,280,780 B1 | 8/2001 | Degady et al. | |
| 6,284,291 B1 | 9/2001 | Siecke et al. | |
| 6,306,429 B1 | 10/2001 | Bealin-Kelly | |
| 6,375,997 B1 | 4/2002 | Sheen et al. | |
| 6,432,441 B1 | 8/2002 | Bealin-Kelly et al. | |
| 6,472,001 B1 | 10/2002 | Bunkers et al. | |
| 6,491,540 B1 | 12/2002 | Barreca | |
| 6,528,102 B1 | 3/2003 | Coyle et al. | |
| 6,551,643 B2 | 4/2003 | Bernatz et al. | |
| 6,558,727 B2 | 5/2003 | Degady et al. | |
| 6,562,382 B1 | 5/2003 | Corriveau et al. | |
| 6,602,518 B2 | 8/2003 | Seielstad et al. | |
| 6,613,346 B2 | 9/2003 | Seielstad et al. | |
| 6,623,266 B2 | 9/2003 | Jani et al. | |
| 6,652,839 B2 | 11/2003 | Barreca | |
| 6,652,875 B1 | 11/2003 | Bannister | |
| 6,692,778 B2 | 2/2004 | Yatka et al. | |
| 6,733,818 B2 | 5/2004 | Luo et al. | |
| 6,780,844 B1 | 8/2004 | Reynolds | |
| 6,846,495 B2 | 1/2005 | Dobrozsi et al. | |
| 6,846,500 B1 | 1/2005 | Luo et al. | |
| 6,869,614 B2 | 3/2005 | Barreca | |
| 6,949,264 B1 | 9/2005 | McGrew et al. | |
| 7,108,885 B2 | 9/2006 | Serpelloni | |
| 2002/0004083 A1 | 1/2002 | Yatka et al. | |
| 2002/0051836 A1 | 5/2002 | Yatka et al. | |
| 2002/0102333 A1 | 8/2002 | Klug et al. | |
| 2002/0136812 A1 | 9/2002 | Degady et al. | |
| 2002/0142059 A1 | 10/2002 | Jani et al. | |
| 2002/0192330 A1 | 12/2002 | Bunkers et al. | |
| 2003/0008062 A1 | 1/2003 | Day et al. | |
| 2003/0059501 A1 | 3/2003 | Rivier | |
| 2003/0072841 A1 | 4/2003 | Rajaiah et al. | |
| 2003/0138518 A1 | 7/2003 | Kiefer et al. | |
| 2003/0190397 A1 | 10/2003 | Serpelloni | |
| 2003/0198713 A1 | 10/2003 | Clark et al. | |
| 2004/0037788 A1 | 2/2004 | Barreca | |
| 2004/0037924 A1 | 2/2004 | Jani et al. | |
| 2004/0037925 A1 | 2/2004 | Jani et al. | |
| 2004/0058033 A1 | 3/2004 | Sozzi et al. | |
| 2004/0096544 A1 | 5/2004 | Yatka et al. | |
| 2004/0105823 A1 | 6/2004 | Kamasaka et al. | |
| 2004/0126472 A1 | 7/2004 | Soldani | |
| 2004/0131751 A1 | 7/2004 | Dekker et al. | |
| 2004/0180110 A1 | 9/2004 | Mistry | |
| 2004/0234459 A1 | 11/2004 | Faust et al. | |
| 2005/0008732 A1 | 1/2005 | Gebreselassie et al. | |
| 2005/0019376 A1 | 1/2005 | McNally et al. | |
| 2005/0063922 A1 | 3/2005 | Reynolds et al. | |
| 2005/0089481 A1 * | 4/2005 | Yamanaka et al. | 424/50 |

| | | | |
|---|---|---|---|
| 2005/0100633 | A1 | 5/2005 | Bunkers et al. |
| 2005/0112236 | A1 | 5/2005 | Boghani et al. |
| 2005/0170041 | A1 | 8/2005 | Abraham et al. |
| 2005/0175733 | A1 | 8/2005 | Thorengaard et al. |
| 2005/0260317 | A1 | 11/2005 | Cotten et al. |
| 2005/0260329 | A1 | 11/2005 | Yusuf et al. |
| 2006/0024354 | A1 | 2/2006 | Barreca |
| 2006/0100398 | A1 | 5/2006 | Shaffer et al. |
| 2006/0188612 | A1 | 8/2006 | Lorenzi |
| 2007/0087100 | A1 | 4/2007 | Fornaguera |
| 2007/0104828 | A1 | 5/2007 | Fornaguera |
| 2007/0104830 | A1 | 5/2007 | Fornaguera |
| 2007/0122528 | A1 | 5/2007 | Cathenaut et al. |
| 2007/0148285 | A1 | 6/2007 | Yang |
| 2007/0160707 | A1 | 7/2007 | Garcia |

FOREIGN PATENT DOCUMENTS

| | | | |
|---|---|---|---|
| CA | 2612172 | A1 | 12/2007 |
| EP | 0086856 | | 8/1983 |
| EP | 0320580 | | 6/1989 |
| EP | 0446170 | B1 | 12/1994 |
| EP | 0724837 | | 8/1996 |
| EP | 0806151 | | 11/1997 |
| EP | 0944331 | | 9/1999 |
| EP | 1003475 | | 5/2000 |
| EP | 1004594 | | 5/2000 |
| EP | 1151673 | | 11/2001 |
| EP | 1425976 | | 6/2004 |
| GB | 2042969 | | 10/1980 |
| GB | 2177587 | | 1/1987 |
| JP | 1951-5888 | | 9/1951 |
| JP | 04179445 | | 6/1992 |
| JP | 4179445 | A | 6/1992 |
| RU | 2239413 | C1 | 11/2004 |
| WO | 8800463 | A1 | 1/1988 |
| WO | 9206160 | A1 | 4/1992 |
| WO | 9508925 | | 4/1995 |
| WO | 9619193 | A1 | 6/1996 |
| WO | 9702011 | A1 | 1/1997 |
| WO | 9706695 | | 2/1997 |
| WO | 9726798 | | 7/1997 |
| WO | 9818339 | A1 | 5/1998 |
| WO | 9823165 | A1 | 6/1998 |
| WO | 9824325 | | 6/1998 |
| WO | 9829088 | A1 | 7/1998 |
| WO | 9840406 | A1 | 9/1998 |
| WO | 9927798 | A1 | 6/1999 |
| WO | 9933352 | A1 | 7/1999 |
| WO | 0006127 | | 2/2000 |
| WO | 0019977 | | 4/2000 |
| WO | 0035298 | A1 | 6/2000 |
| WO | 0057842 | A2 | 10/2000 |
| WO | 0062762 | A1 | 10/2000 |
| WO | 0167884 | | 9/2001 |
| WO | 02056698 | | 7/2002 |
| WO | 2004028266 | | 4/2004 |
| WO | 2005037238 | A2 | 4/2005 |
| WO | 2005048728 | | 6/2005 |
| WO | 2005058263 | A1 | 6/2005 |
| WO | 2005065461 | | 7/2005 |
| WO | 2006026298 | | 3/2006 |
| WO | 2006037319 | | 4/2006 |
| WO | 2006039519 | | 4/2006 |
| WO | 2006056013 | A1 | 6/2006 |
| WO | 2006077480 | | 7/2006 |
| WO | 2006127618 | A2 | 11/2006 |
| WO | 2007079333 | | 7/2007 |

OTHER PUBLICATIONS

Lieberman, Herbert A, Liberman, Leon; "Pharmaceutical Dosage Forms"; Tablets; vol. 1, pp. 386-399.

Jackson, E.B.; "Cerelose—The Confectionery Industry's Natural Sweetener"; Confectionery Manufacture and Marketing; vol. 28 Jun. 1991, No. 6, pp. 20-22.

Jackson, E.B; "Cerelose—It's role in improved Confectionery"; Confectionery Production; vol. 57 Jan. 1991, No. 1, pp. 79-91.

Hintlain, F.; "Filled Hard Candy"; Manufacturing Confectioner; vol. 75, Oct. 1995, No. 10, pp. 61-66.

Hume, J; "Notebook of a Practical Confectioner V. Continuation of Recipes for Centres"; Confectionery Production; vol. 44 Jan. 1978, pp. 18, 20.

Centres for High Boilings—Fruit Pulp, Caramel, Treacle or Powder; by "Sweetmaker" Confectionery Production; vol. 48, Aug. 1982, pp. 344-345.

Long, T; "Producing Centre Filled Hard Candy, Chewing Gum and Toffees"; Candy and Snack Industry; vol. 145 Nov. 1980, No. 11, pp. 34, 37.

Gonze, M.; "High Purity Erythritol for New Health Food Applications"; ZFL, Internationale Zeitschrift Fur Lebensmittel-Tichnik, Marketing, Verpackung and Analytik; vol. 47 1996, No. 11, pp. 66-68.

McIntyre, M. "Isomalt as an International Sugar Replacer"; Food Ingredients and Analysis International; vol. 23 2001, No. 6, pp. 35-36.

Deis, R.; "Polyols in Confectionery"; Manufacturing Confectioner; vol. 80 Oct. 2000, No. 10, pp. 53-57.

Hyvoenen, L.; Koivistoinen, P.; Voirol, F.; "Food Technological Evaluation of Xylitol"; Advances in Food Research, vol. 28 1982, pp. 373-403.

Fritz, Douglas P; "Using Confectionery Equipment to Manufacture Chewing Gum"; Manufacturing Confectioner; Nov. 2000, vol. 80, No. 11, pp. 45-48.

Rogers, P; "Helping the Medicine Go Down"; vol. 166 2001, No. 5, pp. 36-40.

"Product Parade"; Candy Industry; Dec. 1991, p. 10.

Honpo, Senjakuame; "Orange Pure Sherbet Candy; Lemon Pure Sherbet Candy Manufacturer"; International Product Alert; Nov. 1991, vol. 8, No. 21.

Shokuhin, Kanebo; "Ninja Club"; International Product Alert, Dec. 1986, Report No. 044453.

Mega Warheads Fruit Flavored Candy—Sour Lemon; Fruit Flavored Candy—Sour Apple; Fruit Flavored Candy—Hot Grape; Fruit Flavored Candy—Hot Cherry, by Foreign Candy Co., Inc.; Product Alert; Jun. 1991, Report No. 096490.

Matlow, Swizzels; "Stingers Taffy Bar—Lemon' Raspberry; Fruit Punch" Nov. 1996, Report 120966.

"Calpis Candy—Assortment by Kanro" Japanscan; May 2000, Report 193961.

Kacena, Radka; Hard Coat Painting; The Manufacturing Confectioner, Oct. 1997; pp. 41-77.

Kanro 10 Tsubu Hinyari Suika Nodoame 10 Candy by Kanro; Jul. 2002, Report 242381.

Warner Lambert Co., "Freshen-up Peppermint Gum; Freshen-up Fruit Gum", Aug. 23, 1982, Report No. 010075, http://www.productscan.com/search/fullrecord.cfm?frprt=9657.

Warner Lambert Co., "Freshen-up Fruit Gum", Feb. 4, 1980, Report No. 000339, http://www.productscan.com/search/fullrecord.cfm?frprt=336.

Warner Lambert Co., "Chewels Sugarless Gum", Oct. 17, 1983, Report No. 018172, http://www.productscan.com/search/fullrecord.cfm?frprt=11085.

P. Shen et al., "Reminerilzation of enamel subsurface lesions by suar-free chewing gum containing casein phosphopeptide-amorphous calcium phosphate" J of Dental Research, 80:12; 2066-2070.

E.C. Reynolds, "Dairy Products and Dental Health", Proceedings of the Nutrition Society of Australia; 19:95-102 (1995).

* cited by examiner

CALCIUM PHOSPHATE COMPLEX AND SALTS IN ORAL DELIVERY SYSTEMS

CROSS-REFERENCE TO RELATED APPLICATIONS

This application claims the benefit of U.S. Provisional Application No. 60/789,525, filed Apr. 5, 2006, and U.S. Provisional Application No. 60/789,528, filed Apr. 5, 2006, the contents both of which are incorporated herein by reference.

FIELD

The present invention relates to methods and compositions for remineralizing tooth enamel of mammals. The methods employ oral delivery systems, such as chewing gum or confectionery compositions, for delivery of a phosphopeptide or phosphoprotein stabilized calcium phosphate or calcium fluoride phosphate complex. The oral delivery systems additionally include a calcium and/or phosphate salt.

BACKGROUND

The formation of dental caries in teeth has been well studied. Although the use of fluorides has decreased the prevalence of dental caries, the disease continues to remain a public health problem. Caries are understood to result from the accumulation of plaque on the teeth and the production of organic acids (plaque acids) when plaque microorganisms ferment sugars and starches in food. Before being washed away by saliva, the acids accumulate in the plaque long enough to lower the pH and to cause some of the enamel, a calcium-phosphorous mineral known as hydroxyapatite, to dissolve, that is, demineralize, which can lead to dental caries (tooth decay), and sensitivity.

Efforts have been made over the years to address the problem of dissolution or demineralization of tooth enamel and the resultant formation of dental caries. Casein phosphopeptide-calcium phosphate complexes are known to have anti-cariogenic teeth strengthening effects when used as dentifrices. The complexes, also known as CPP-ACP complexes or calcium casein peptone-calcium phosphate, are calcium phosphate stabilized by casein phosphopeptides. CPP-ACP counteracts demineralization by enhancing remineralization while buffering plaque acid. It acts by localizing calcium and phosphate ions at the tooth surface. CPP-ACP is commercially available under the trade name Recaldent.

U.S. Pat. Nos. 5,130,123 and 5,227,154 teach casein phosphopeptides in prevention of dental caries. International Publication No. WO 98/40406 teaches phosphopeptide-calcium phosphate complexes to provide anti-caries efficacy. U.S. Pat. Nos. 6,846,500 and 6,733,818 disclose chewing gum and confectionery products containing a combination of casein phosphopeptide-amorphous calcium phosphate with sodium bicarbonate. International Publication No. WO 2006/135982 discloses super-loaded complexes of amorphous calcium phosphate or amorphous calcium fluoride phosphate stabilized by a phosphopeptide or a phosphoprotein.

Dental caries, however, continues to be a problem in many communities. The high cost to individuals and the community in treating dental caries has necessitated the development of new caries-preventive products.

There is a need, therefore, for new methods of promoting remineralization of the tooth enamel of mammals. As many consumers enjoy oral delivery systems, particularly sugared chewing gum and confectionery products, which typically demineralize the teeth, there is a need for products that can provide remineralization of the tooth enamel of mammals.

SUMMARY

In some embodiments there is an oral delivery system including a phosphopeptide or phosphoprotein stabilized calcium phosphate or calcium fluoride phosphate complex and a salt selected from calcium salts, phosphate salts and combinations thereof.

In some embodiments there is provided a composition including casein phosphopeptide-calcium phosphate and a salt selected from calcium salts, phosphate salts and combinations thereof, wherein upon consumption the composition provides a greater amount of enamel subsurface remineralization in the tooth of a mammal than a composition which is substantially the same as the composition but which is free of casein phosphopeptide-calcium phosphate and the salt.

Some embodiments provide a sugared confectionery composition including a solid portion and a dissolved portion of the solid portion, the solid and the dissolved portions including a confectionery carrier including at least one sugar sweetener, casein phosphopeptide-calcium phosphate and a salt selected from calcium salts, phosphate salts and combinations thereof, the casein phosphopeptide-calcium phosphate being present in amounts of at least about 0.1% by weight of the composition, wherein upon consumption the composition provides a greater amount of enamel subsurface remineralization in the tooth of a mammal than a sugared confectionery composition which is substantially the same as the composition but which is free of casein phosphopeptide-calcium phosphate and the salt.

Some other embodiments provide a sugared confectionery composition including a confectionery carrier which includes at least one sugar sweetener, casein phosphopeptide-calcium phosphate present in amounts of at least about 0.1% by weight of the composition, and a salt selected from calcium salts, phosphate salts and combinations thereof, the salt being present in amounts of about 1% to about 5% by weight of the composition, wherein the composition provides at least about 2.8% enamel subsurface remineralization in the tooth of a mammal upon consumption.

In some embodiments, there is provided a sugared chewing gum composition including a solid portion and a dissolved portion of the solid portion, the solid portion including a gum base, at least one sugar sweetener, casein phosphopeptide-calcium phosphate and a salt selected from calcium salts, phosphate salts and combinations thereof, and the dissolved portion including at least one sugar sweetener, casein phosphopeptide-calcium phosphate and the salt, wherein the casein phosphopeptide-calcium phosphate is present in amounts of at least about 0.1% by weight of the composition, and wherein upon consumption the composition provides a greater amount of enamel subsurface remineralization in the tooth of a mammal than a sugared chewing gum composition which is substantially the same as the composition but which is free of casein phosphopeptide-calcium phosphate and the salt.

Some embodiments provide a sugared chewing gum composition including a gum base, at least one sugar sweetener, casein phosphopeptide-calcium phosphate present in amounts of at least about 0.1% by weight of the composition, and a salt selected from calcium salts, phosphate salts and combinations thereof, the salt being present in amounts of about 1% to about 5% by weight of the composition, wherein the composition provides at least about 2.8% enamel subsurface remineralization in the tooth of a mammal upon consumption.

Some other embodiments provide a method of remineralizing enamel subsurface lesions in the tooth of a mammal, which includes the steps of:

(a) applying an oral delivery system into the oral cavity of the mammal, wherein the delivery system includes:
  (i) a phosphopeptide or phosphoprotein stabilized calcium phosphate or calcium fluoride phosphate complex; and
  (ii) a salt selected from calcium salts, phosphate salts and combinations thereof; and
(b) retaining the delivery system in the oral cavity for a time sufficient to remineralize enamel subsurface lesions in the tooth of the mammal by an amount greater than that provided by consuming a delivery system which is substantially the same as the delivery system but which is free of said phosphopeptide or phosphoprotein stabilized calcium phosphate or calcium fluoride phosphate complex and the salt for the same period of time.

Still other embodiments provide a kit for remineralizing enamel subsurface lesions in the tooth of a mammal including:

(a) an oral delivery system including:
  (i) a phosphopeptide or phosphoprotein stabilized calcium phosphate or calcium fluoride phosphate complex; and
  (ii) a salt selected from calcium salts, phosphate salts and combinations thereof,
    wherein upon consumption the delivery system provides a greater amount of enamel subsurface remineralization in the tooth of a mammal than a delivery system which is substantially the same as the delivery system but which is free of said phosphopeptide or phosphoprotein stabilized calcium phosphate or calcium fluoride phosphate complex and the salt;
(b) a set of instructions for using the oral delivery system; and
(c) a package for housing the oral delivery system and the set of instructions.

DETAILED DESCRIPTION

Figure 1:
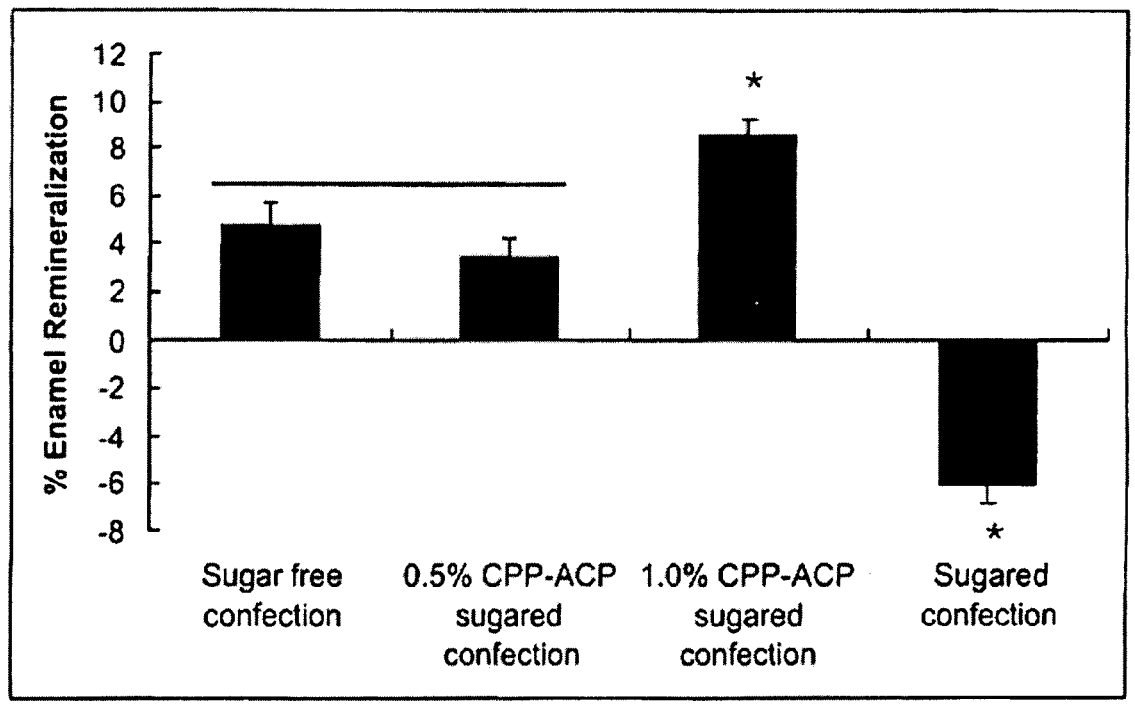
FIG. 1 is a graphical representation of the percentage of remineralization of enamel subsurface lesions provided by two sugared confectionery compositions including CPP-ACP according to the present invention as compared to a sugared control and a sugar-free control.

Embodiments described herein provide oral delivery systems, such as chewing gum and confectionery products, containing a phosphopeptide or phosphoprotein stabilized calcium phosphate or calcium fluoride phosphate complex, which is an anticaries agent, and a calcium and/or phosphate salt. Desirably, the phosphopeptide stabilized calcium phosphate is casein phosphopeptide-calcium phosphate (CPP-ACP). Embodiments described herein also provide methods of employing such oral delivery systems to improve the dental health of mammals. Specifically, upon consumption, the oral delivery systems promote tooth enamel remineralization, particularly remineralization of enamel subsurface lesions in the tooth.

A variety of different oral delivery systems may be used to deliver the tooth enamel remineralization benefits described herein. For example, suitable oral delivery systems include, but are not limited to, confectioneries, chewing gum, gels, dentifrices, toothpaste, mouthwash, mouth rinse, mouth spray, edible film, beverages, food, and the like.

In some embodiments, for instance, the oral delivery system may be a confectionery or chewing gum composition. These compositions may be sugared, i.e., containing one or more sugar sweeteners, or sugar-free, i.e., containing only sugarless sweeteners. In particular, some embodiments described herein provide sugared confectionery or chewing gum compositions for remineralizing the tooth enamel of mammals, particularly humans. Sugared confectionery compositions may include a confectionery carrier, which includes at least one sugar sweetener, CPP-ACP and a calcium and/or phosphate salt. Similarly, sugared chewing gum compositions may include a gum base, at least one sugar sweetener, CPP-ACP and a calcium and/or phosphate salt. Desirably, the CPP-ACP is present in amounts of at least about 0.1% by weight of the confectionery or chewing gum composition.

CPP-ACP can also be used with other oral care actives as part of a multi-functional oral care product. These other oral care actives can include, but are not limited to whitening actives, antimicrobial actives, breath freshening actives, desensitizing actives, and other remineralizing actives. Upon consumption, the oral delivery systems described herein provide a greater amount of enamel subsurface remineralization in the tooth of a mammal than an oral delivery system that is substantially the same but free of CPP-ACP and the calcium and/or phosphate salt.

By "substantially the same", it is meant that the composition contains the same components as the inventive composition but the amounts of some or all of the components may vary slightly to make up for the missing amount of CPP-ACP and the calcium and/or phosphate salt contained in the inventive composition.

Methods of remineralizing enamel subsurface lesions in the tooth of a mammal also are described herein employing the various oral delivery systems.

As used herein the transitional term "comprising," (also "comprises," etc.) which is synonymous with "including," "containing," or "characterized by," is inclusive or open-ended and does not exclude additional, unrecited elements or method steps, regardless of its use in the preamble or the body of a claim.

As used herein, the terms "bubble gum" and "chewing gum" are used interchangeably and are both meant to include any gum compositions.

As used herein, the term "center-fill" refers to the innermost region of a center-fill gum or confectionery product. The term "center-fill" does not imply symmetry of a gum or confectionery product, only that the "center-fill" is within another region of the product. In some embodiments, more than one center-fill may be present.

As used herein, the term "gum region" or "confectionery region" refers to a region of a center-fill gum or confectionery product, respectively, that may be adjacent to or at least partially surrounding the center-fill, or innermost, region. In some embodiments, the gum region or confectionery region is an intermediate region.

As used herein, the terms "coating" or "coating region" are used to refer to the outermost region of a center-fill gum or confectionery product.

As used herein, the terms "surround," "surrounding," and the like are not limited to encircling. These terms may refer to enclosing or confining on all sides, encircling or enveloping, and are not limited to symmetrical or identical thicknesses for a region in a center-fill gum or confectionery product.

Oral Delivery Systems

Oral delivery systems generally include any products that are retained in the oral cavity for a sufficient time to contact the dental surfaces and exhibit the desired activity. The oral delivery systems described herein promote remineralization of the tooth enamel. These delivery systems include a phosphopeptide or phosphoprotein stabilized calcium phosphate or calcium fluoride phosphate complex and a calcium and/or phosphate salt. In some embodiments, the phosphopeptide is casein phosphopeptide, which may maintain the calcium phosphate or calcium fluoride phosphate in a stabilized and soluble form. Desirably, the complex is CPP-ACP.

The casein phosphopeptides that are active in forming the complexes do so whether or not they are part of a full-length casein protein. The active casein phosphopeptides formed by tryptic digestion have been set forth in U.S. Pat. No. 5,015,628 and include peptides Bos $\alpha_{s1}$-casein X-5P (f59-79) [1], Bos β-casein X-4P (f1-25) [2], Bos $\alpha_{s2}$-casein X-4P (f46-70) [3] and Bos $\alpha_{s2}$-casein X-4P (f1-21) [4] as follows:

[1] $Gln^{59}$-Met-Glu-Ala-Glu-Ser(P)-Ile-Ser(P)-Ser(P)-Ser(P)-Glu-Glu-Ile-Val-Pro-Asn-Ser(P)-Val-Glu-Gln-$Lys^{79}$ $\alpha_{s1}$(59-79)

[2] $Arg^{1}$-Glu-Leu-Glu-Glu-Leu-Asn-Val-Pro-Gly-Glu-Ile-Val-Glu-Ser(P)-Leu-Ser(P)-Ser(P)-Ser(P)-Glu-Glu-Ser-Ile-Thr-$Arg^{25}$ β(1-25)

[3] $Asn^{46}$-Ala-Asn-Glu-Glu-Glu-Tyr-Ser-Ile-Ser(P)-Ser(P)-Ser(P)-Glu-Glu-Ser(P)-Ala-Glu-Val-Ala-Thr-Glu-Glu-Val-$Lys^{70}$ αs2(46-70)

[4] $Lys^{1}$-Asn-Thr-Met-Glu-His-Val-Ser(P)-Ser(P)-Ser(P)-Glu-Glu-Ser-Ile-Ile-Ser(P)Gln-Glu-Thr-Tyr-$Lys^{21}$ αs2(1-21)

Other casein phosphopeptides that have activity in forming the complexes are those peptides containing the sequences Ser(P)-Xaa-Glu/Ser(P), in which Ser(P) represents a phosphoseryl residue. Therefore, the phosphopeptides or phosphoproteins active in stabilizing the calcium phosphate or calcium fluoride phosphate complexes are those containing the sequence -A-B-C-, in which A is a phosphamino acid, such as phosphoserine, B is any amino acid including a phosphoamino acid and C is one of glutamate, aspartate or phosphoamino acid.

In some embodiments, the complex, such as, for example, CPP-ACP, is present in amounts of at least about 0.1% by weight of the oral delivery system. The complex may be present in amounts of up to about 2.5% by weight of the oral delivery system in some embodiments. More particularly, in some embodiments, the complex may be present in amounts of about 1% to about 2.5% by weight of the oral delivery system.

In some embodiments, the complex, such as CPP-ACP, is incorporated into the oral delivery systems in a modified release form. For instance, CPP-ACP may be encapsulated to provide modified release characteristics to the component. In general, partially or completely encapsulating CPP-ACP with an encapsulating material may delay release of the ingredient during consumption of the oral delivery system, thereby delaying when the ingredient becomes available inside the consumer's mouth, available to react or mix with another ingredient, and/or available to provide some functional or therapeutic benefit. This can be particularly true when the ingredient is water soluble or at least partially water soluble.

In some embodiments, CPP-ACP may be used in its encapsulated and/or its unencapsulated (sometimes referred to as "free") forms. In confectionery embodiments, for example, CPP-ACP may be incorporated into one or more regions of a center-fill product in its encapsulated and/or unencapsulated forms. For example, in a center-fill candy, encapsulated CPP-ACP may be included in the confectionery region and unencapsulated CPP-ACP may be included in the center-fill region. Alternatively, in some embodiments a combination of encapsulated CPP-ACP and unencapsulated CPP-ACP may be included in the same region of the product. The encapsulated and unencapsulated forms may be used in the same or different amounts.

Suitable encapsulating materials for CPP-ACP may include water insoluble polymers, co-polymers, or other materials capable of forming a strong matrix, solid coating, or film as a protective barrier with or for the ingredient. In some embodiments, the encapsulating material may completely surround, coat, cover, or enclose the CPP-ACP. In other embodiments, the encapsulating material may only partially surround, coat, cover, or enclose the CPP-ACP. Different encapsulating materials may provide different release rates or release profiles for the encapsulated CPP-ACP. In some embodiments, encapsulating material used in a delivery system may include one or more of the following: polyvinyl acetate, polyethylene, crosslinked polyvinyl pyrrolidone, polymethylmethacrylate, polylactidacid, polyhydroxylkanoates, ethylcellulose, polyvinyl acetatephthalate, polyethylene glycol esters, methacrylicacid-co-methylmethacrylate, ethylene-vinylacetate (EVA) copolymer, and the like, and combinations thereof.

A more detailed discussion of suitable encapsulating materials and techniques is provided in assignee's co-pending PCT Application No. PCT/US06/19761, which published as International Publication No. WO 2006/127618, which is incorporated by reference herein in its entirety.

The oral delivery systems also include a salt selected from calcium salts, phosphate salts and combinations thereof. The salts release and deliver calcium and/or phosphate ions to the surface of the tooth upon administration of the oral delivery system in the oral cavity of the individual, which promotes remineralization of the tooth enamel. The calcium and/or phosphate salt is a separate and additional salt apart from the phosphopeptide or phosphoprotein stabilized calcium phosphate or calcium fluoride phosphate complex.

Suitable calcium salts include, but are not limited to, calcium chloride, calcium lactate, calcium sulfate, calcium carbonates, calcium phosphates, such as monocalcium phosphate, dicalcium phosphate anhydrous, dicalcium phosphate dihydrate, α-tricalcium phosphate, octacalcium phosphate and tetracalcium phosphate, calcium glutareate, calcium malate, calcium citrate, calcium gluconate, calcium glycerophosphate, calcium fumarate, calcium hydroxide, calcium oxide and combinations thereof.

Suitable phosphate salts include, but are not limited to, neutral, monobasic and dibasic phosphate salts. For instance, sodium phosphate may be employed.

In general, the salts may be present in amounts of about 1% to about 5% by weight of the oral delivery system. Calcium salts may be present in amounts of about 1.5% to about 3% by weight of the oral delivery system, more specifically about 1.6% to about 2.8% by weight of the oral delivery system. Phosphate salts may be present in amounts of about 1% to about 4% by weight of the oral delivery system, specifically about 1.5% to about 4% by weight of the oral delivery system, more specifically about 1.6% to about 3% by weight of the oral delivery system, and even more specifically about 1.2% to about 1.8% by weight of the oral delivery system.

In some embodiments, the oral delivery systems described above may provide at least about 2.8% enamel subsurface remineralization of the tooth. In particular, some embodiments including at least about 0.5% by weight CPP-ACP may provide at least about 2.8% enamel subsurface remineralization. Some other embodiments containing at least about 1% CPP-ACP may provide at least about 8% enamel subsurface remineralization.

Some embodiments described herein, which include at least about 0.1% CPP-ACP, at least about 1.6% calcium lactate and at least about 1.5% phosphate salts, such as sodium phosphates, provide at least about 7% enamel subsurface remineralization. In some other embodiments, oral delivery systems containing at least about 0.1% CPP-ACP, at least about 2.8% calcium lactate and at least about 1.7% phosphate salts, such as sodium phosphates, provide at least about 12.5% enamel subsurface remineralization. Furthermore, the oral delivery systems described herein may provide at least about 0.35% mineralization of sound tooth enamel, and in some embodiments, at least about 0.5% mineralization of sound tooth enamel.

In contrast, traditional oral delivery systems that are free of a phosphopeptide or phosphoprotein stabilized calcium phosphate or calcium fluoride phosphate complex and calcium and/or phosphate salts tend to demineralize the tooth enamel, particularly when the delivery system is a sugared product. For instance, it has been found that sugared confectionery compositions that are substantially the same as those described herein, but free of CPP-ACP, produce about 6% demineralization of enamel subsurface lesions in the tooth. It also has been found that sugared confectionery compositions that are substantially the same as those described herein, but free of CPP-ACP and calcium and/or phosphate salts, produce about 5.2% demineralization of enamel subsurface lesions in the tooth. In view thereof, it was unexpected that a sugared confectionery composition could promote remineralization of tooth enamel.

Some embodiments described herein provide at least about 12% more remineralization than comparable sugared compositions that are free of CPP-ACP and calcium and/or phosphate salts. Further, some embodiments provide at least about 18% more remineralization than such comparable compositions. In some embodiments, the oral delivery systems even promote a greater amount of remineralization of tooth enamel than sugar-free compositions that are substantially the same but free of CPP-ACP and the salt.

Optional additives also may be included in the oral delivery systems, such as chelating agents, food-grade acids, peroxides, plasticizers, softeners, emulsifiers, waxes, fillers, bulking agents (carriers, extenders, bulk sweeteners), intense sweeteners, mineral adjuvants, flavor agents and coloring agents, physiological cooling agents, warming agents, tingling agents, antioxidants, acidulants, thickeners, medicaments, oral care actives, such as other remineralization agents, antimicrobials and tooth whitening agents, as described in assignee's co-pending U.S. patent application Ser. No. 10/901,511, filed on Jul. 29, 2004 and entitled "Tooth Whitening Compositions and Delivery Systems Therefor," which is incorporated herein by reference in its entirety, and the like, and mixtures thereof. Some of these additives may serve more than one purpose.

Some embodiments may include chelating agents. Chelating agents strongly interact with metal ions, such as the calcium found in the cell walls of mouth bacteria. Chelating agents can also disrupt plaque by removing calcium from the calcium bridges which help hold this biomass intact. One group of agents suitable for use as chelating agents in the oral delivery systems are polyphosphates. In some embodiments, the chelating agent is a phosphate salt selected from the following: pyrophosphates, triphosphates, polyphosphates, polyphosphonates and combinations thereof. The chelating agent can be a dialkali metal pyrophosphate salt, a tetra alkali polyphosphate salt or a combination thereof. For example, in some embodiments, the chelating agent can be selected from the following: tetrasodium pyrophosphate, tetrapotassium pyrophosphate, sodium tripolyphosphate and combinations of these. Other chelating agents that can be employed in the oral delivery systems may include tartaric acid and salts thereof, citric acid and alkali metal citrates and mixtures thereof.

Food-grade acids include, but are not limited to, acetic acid, adipic acid, ascorbic acid, butyric acid, citric acid, formic acid, fumaric acid, glyconic acid, lactic acid, malic acid, phosphoric acid, oxalic acid, succinic acid, tartaric acid and combinations thereof. Although it may be desirable to include food-grade acids in some embodiments, other embodiments may be free of acid.

In some embodiments, the oral delivery system may be free of added sodium bicarbonate. More specifically, some known delivery systems have included 0.1% to 15% by weight sodium bicarbonate with CPP-ACP to reduce plaque upon consumption, as described in U.S. Pat. No. 6,846,500, referred to above. Sodium bicarbonate also may be used as a filler. Embodiments described herein may be free of added sodium bicarbonate or contain less than 0.1% by weight sodium bicarbonate. Similarly, some embodiments described herein may be free of any mineral fillers. Other embodiments, however, may include sodium bicarbonate.

As mentioned above, any commonly used oral delivery system may be employed to deliver the phosphopeptide or phosphoprotein stabilized calcium phosphate or calcium fluoride phosphate complexes and calcium and/or phosphate salts described herein. Suitable oral delivery systems include, but are not limited to, confectioneries, chewing gum, gels, dentifrices, toothpaste, mouthwash, mouth rinse, mouth spray, edible film, beverages and food, among others. Examples of several of these oral delivery systems are described in more detail below.

Confectionery Compositions

Some embodiments described herein provide confectionery compositions, which include confections other than chewing gum compositions. The confectionery compositions include a phosphopeptide or phosphoprotein stabilized calcium phosphate or calcium fluoride phosphate complex, such as CPP-ACP, which is an anticaries agent, and a calcium and/or phosphate salt. The confectionery compositions also include a confectionery carrier. Some embodiments provide sugared confectionery compositions, which include at least one sugar sweetener. The sugared confectionery compositions also may include sugarless sweeteners in addition to the sugar sweeteners. Other embodiments provide sugar-free confectionery compositions, which include only sugarless sweeteners. The confectionery compositions described herein promote remineralization of the tooth enamel to a greater extent than confectionery compositions that are substantially the same as the inventive compositions but free of CPP-ACP and the calcium and/or phosphate salt.

Confectionery compositions may be provided in a variety of different forms, such as, for example, hard candy, soft candy, cotton candy, pressed tablets, lozenges, nougats, caramels, frappes and taffies. The confectionery compositions also may include at least one flavor and a variety of optional additives.

The confectionery carrier includes at least one sweetener. Saccharides, including sugar and/or sugarless sweeteners, may be employed. Although sugared confectionery compositions may be free of sugarless sweetening agents, some embodiments may include sugarless bulk sweeteners and/or intense sweeteners in addition to the at least one sugar sweetener. Sugar-free confectionery compositions, however, include only sugarless sweeteners.

Suitable sugar sweeteners for use in the confectionery carrier include mono-saccharides, di-saccharides and poly-saccharides such as but not limited to, sucrose (sugar), dextrose, maltose, dextrin, xylose, ribose, glucose, mannose, galactose, fructose (levulose), invert sugar, fructo oligo saccharide syrups, partially hydrolyzed starch, corn syrup solids and mixtures thereof. In addition to the sugar sweetener, the confectionery carrier may include a variety of optional components selected from well-known carriers in the art. Selection of suitable carriers depends upon the type of confection being prepared.

Suitable sugarless bulk sweeteners include sugar alcohols (or polyols) such as, but not limited to, sorbitol, xylitol, mannitol, galactitol, maltitol, hydrogenated isomaltulose (ISOMALT), lactitol, erythritol, hydrogenated starch hydrolysates, and mixtures thereof.

Suitable hydrogenated starch hydrolysates include those disclosed in U.S. Pat. No. 4,279,931 and various hydrogenated glucose syrups and/or powders which contain sorbitol, maltitol, hydrogenated disaccharides, hydrogenated higher polysaccharides, or mixtures thereof. Hydrogenated starch hydrolysates are primarily prepared by the controlled catalytic hydrogenation of corn syrups. The resulting hydrogenated starch hydrolysates are mixtures of monomeric, dimeric, and polymeric saccharides. The ratios of these different saccharides give different hydrogenated starch hydrolysates different properties. Mixtures of hydrogenated starch hydrolysates, such as LYCASIN®, a commercially available product manufactured by Roquette Freres of France, and HYSTAR®, a commercially available product manufactured by SPI Polyols, Inc. of New Castle, Del., are also useful.

In some embodiments, high-intensity sweeteners may be used. Without being limited to particular sweeteners, representative categories and examples include:

(a) water-soluble sweetening agents such as dihydrochalcones, monellin, stevia, steviosides, rebaudioside A, glycyrrhizin, dihydroflavenol, and sugar alcohols such as sorbitol, mannitol, maltitol, xylitol, erythritol and L-aminodicarboxylic acid aminoalkenoic acid ester amides, such as those disclosed in U.S. Pat. No. 4,619,834, which disclosure is incorporated herein by reference, and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and mixtures thereof;

(c) dipeptide based sweeteners, such as L-aspartic acid derived sweeteners, such as L-aspartyl-L-phenylalanine methyl ester (Aspartame) and materials described in U.S. Pat. No. 3,492,131, L-alphaaspartyl-N-(2,2,4,4-tetramethyl-3-thietanyl)-D-alaninamide hydrate (Alitame), N—[N-(3,3-dimethylbutyl)-L-aspartyl]-L-phenylalanine 1-methyl ester (Neotame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, and mixtures thereof;

(d) water-soluble sweeteners derived from naturally occurring water-soluble sweeteners, such as chlorinated derivatives of ordinary sugar (sucrose), e.g., chlorodeoxysugar derivatives such as derivatives of chlorodeoxysucrose or chlorodeoxygalactosucrose, known, for example, under the product designation of Sucralose; examples of chlorodeoxysucrose and chlorodeoxygalactosucrose derivatives include but are not limited to: 1-chloro-1'-deoxysucrose; 4-chloro-4-deoxy-alpha-D-galactopyranosyl-alpha-D-fructofuranoside, or 4-chloro-4-deoxygalactosucrose; 4-chloro-4-deoxy-alpha-D-galactopyranosyl-1-chloro-1-deoxy-beta-D-fructo-f uranoside, or 4,1'-dichloro-4,1'-dideoxygalactosucrose; 1',6'-dichloro 1',6'-dideoxysucrose; 4-chloro-4-deoxy-alpha-D-galactopyranosyl-1,6-dichloro-1,6-dideoxy-beta-D-fructofuranoside, or 4,1',6'-trichloro-4,1',6'-trideoxygalactosucrose; 4,6-dichloro-4,6-dideoxy-alpha-D-galactopyranosyl-6-chloro-6-deoxy-beta-D-fructofuranoside, or 4,6,6'-trichloro-4,6,6'-trideoxygalactosucrose; 6,1',6'-trichloro-6,1',6'-trideoxysucrose; 4,6-dichloro-4,6-dideoxy-alpha-D-galactopyranosyl-1,6-dichloro-1,6-dideox y-beta-D-fructofuranoside, or 4,6,1',6'-tetrachloro 4,6,1',6'-tetradeoxygalacto-sucrose; and 4,6,1',6'-tetradeoxy-sucrose, and mixtures thereof;

(e) protein based sweeteners such as *thaumaoccous danielli* (Thaumatin I and II) and talin;

(f) the sweetener monatin (2-hydroxy-2-(indol-3-ylmethyl)-4-aminoglutaric acid) and its derivatives; and (g) the sweetener Lo han guo (sometimes also referred to as "Lo han kuo").

The intense sweetening agents may be used in many distinct physical forms well-known in the art to provide an initial burst of sweetness and/or a prolonged sensation of sweetness. Without being limited thereto, such physical forms include free forms, such as spray dried, powdered, beaded forms, encapsulated forms, and mixtures thereof. Intense sweeteners optionally may be present in amounts from about 0.001% to about 3%, by weight of the composition, depending upon the sweetener or combination of sweeteners used.

In general, a hard boiled candy confection has a base composed of a mixture of sugar and/or sugarless sweetening agents and other carbohydrate bulking agents kept in an amorphous or glassy condition. In some embodiments, the at least one sweetener itself may act as the carrier for the confectionery composition, or additional carrier components may be employed. Any of the sweeteners provided above may be used. A general discussion of the composition and preparation of hard confections may be found in E. B. Jackson, Ed. "Sugar Confectionery Manufacture", 2nd edition, Blackic Academic & Professional Press, Glasgow UK, (1990), at pages 129-169, as well as in H. A. Lieberman, Pharmaceutical Dosage Forms: Tablets, Volume 1 (1980), Marcel Dekker, Inc., New York, N.Y. at pages 339 to 469, which disclosure is incorporated herein by reference.

Such confectionery compositions may be routinely prepared by conventional methods such as those involving fire cookers, vacuum cookers, and scraped-surface cookers also referred to as high speed atmospheric cookers.

Fire cookers involve the traditional method of making a candy base. In this method, the desired quantity of carbohydrate bulking agent is dissolved in water by heating the agent in a kettle until the bulking agent dissolves. Additional bulking agent may then be added and cooking continued until a final temperature of 145° C. to 156° C. is achieved. The batch is then cooled and worked as a plastic-like mass to incorporate additives such as flavors, colorants and the like.

A high-speed atmospheric cooker uses a heat-exchanger surface which involves spreading a film of candy on a heat exchange surface, the candy is heated to 165° C. to 170° C. in a few minutes. The candy is then rapidly cooled to 100° C. to 120° C. and worked as a plastic-like mass enabling incorporation of the additives, such as flavors, colorants and the like.

In vacuum cookers, the carbohydrate bulking agent is boiled to 125° C. to 132° C., vacuum is applied and additional water is boiled off without extra heating. When cooking is complete, the mass is a semi-solid and has a plastic-like consistency. At this point, flavors, colorants, and other additives are admixed in the mass by routine mechanical mixing operations.

The optimum mixing required to uniformly mix the flavors, colorants and other additives during conventional manufacturing of hard confectionery is determined by the time needed to obtain a uniform distribution of the materials. Normally, mixing times of from 4 to 10 minutes have been found to be acceptable.

Once the candy mass has been properly tempered, it may be cut into workable portions or formed into desired shapes. A variety of forming techniques may be utilized depending upon the shape and size of the final product desired.

Soft candy confectionery compositions includes fondants, caramels toffees, fudge, marshmallows and nougats and the like and may also include jams and jellies. The preparation of soft confectionery compositions, such as nougat, involves conventional methods, such as the combination of two primary components, namely (1) a high boiling syrup, and (2) a relatively light textured frappe, generally prepared from egg albumin, gelatin, vegetable proteins, such as soy derived compounds, milk derived compounds such as milk proteins, and mixtures thereof. A general discussion of the composition and preparation of such confections may be found in E. B. Jackson. Ed. "Sugar Confectionery Manufacture", 2nd edition, Blackie Academic & Professional Press. Glasgow UK (1990), at pages 170-235.

The high boiling syrup, or "bob syrup", of the soft confectionery is relatively viscous and has a higher density than the frappe component, and frequently contains a substantial amount of carbohydrate bulking agent such as a hydrogenated starch hydrolysate. Conventionally, the final nougat composition is prepared by the addition of the "bob syrup" to the frappe under agitation, to form the basic nougat mixture. Further ingredients such as flavoring, additional carbohydrate bulking agent, colorants, preservatives, medicaments, mixtures thereof and the like may be added thereafter also under agitation. A general discussion of the composition and preparation of nougat confections may be found in B. W. Minifie, Chocolate, Cocoa and Confectionery: Science and Technology, 2nd edition, AVI Publishing Co., Inc., Westport, Conn. (1980), at pages 424-425, which disclosure is incorporated herein by reference.

The procedure for preparing the soft confectionery involves known procedures. In general, the frappe component is prepared first and thereafter the syrup component is slowly added under agitation at a temperature of at least about 65° C., and preferably at least about 100° C. The mixture of components is continued to be mixed to form a uniform mixture, after which the mixture is cooled to a temperature below 80° C., at which point, the flavor may be added. The mixture is further mixed for an additional period until it is ready to be removed and formed into suitable confectionery shapes.

Compressed tablet confectionery compositions contain particular materials and are formed into structures under pressure. These confections generally contain sugar, and optionally sugar substitutes, in amounts up to about 95%, by weight of the composition, and typical tablet excipients such as binders and lubricants.

In general, the confectionery carrier is present in amounts of about 5% to about 99% by weight of the confectionery composition. More specifically, the confectionery carrier may be present in amounts of about 80% to about 99% by weight of the confectionery composition. The sweetener generally may be present in amounts of about 5% to about 99% by weight of the confectionery composition.

As described above, CPP-ACP may be present in amounts of about 0.1% to about 2.5% by weight of the confectionery composition. In some embodiments, CPP-ACP may be present in amounts of about 1% to about 2.5% by weight of the composition. The confectionery product formed from the confectionery compositions may contain, for instance, about 38 mg CPP-ACP in some embodiments. In some other embodiments, for example, the confectionery product may contain about 25 mg CPP-ACP and about 150 mg calcium lactate. Such confectionery compositions provide a greater amount of tooth enamel remineralization than confectionery compositions that are substantially the same as the compositions provided by such embodiments but free of CPP-ACP and calcium and/or phosphate salts.

For instance, in some embodiments, sugared confectionery compositions containing at least about 0.5% CPP-ACP provide at least about 2.8% enamel subsurface remineralization. In some other embodiments, sugared confectionery compositions containing at least about 1% CPP-ACP provide at least about 8% enamel subsurface remineralization.

In contrast, traditional sugared confectionery compositions that are free of CPP-ACP tend to demineralize the tooth enamel. In particular, as mentioned above, it has been found that sugared confectionery compositions that are substantially the same as those described herein, but free of CPP-ACP, produce about 6% demineralization of enamel subsurface lesions in the tooth. In view thereof, it was unexpected that a sugared confectionery composition could promote remineralization of tooth enamel.

In some embodiments, sugared confectionery compositions containing at least about 0.1% CPP-ACP, at least about 1.6% calcium lactate and at least about 1.5% phosphate salts provide at least about 7% enamel subsurface remineralization. In some other embodiments, sugared confectionery compositions containing at least about 0.1% CPP-ACP, at least about 2.8% calcium lactate provide and at least about 1.7% phosphate salts provide at least about 12.5% enamel subsurface remineralization. Further, the sugared confectionery compositions of some embodiments provide at least about 0.35% mineralization of sound tooth enamel, and in some embodiments, at least about 0.5% mineralization of sound tooth enamel.

In contrast, traditional sugared confectionery compositions that are free of CPP-ACP, calcium lactate and phosphate salts tend to demineralize the tooth enamel. In particular, it has been found that sugared confectionery compositions that are substantially the same as those described herein, but free of CPP-ACP and calcium and/or phosphate salts, produce about 5.2% demineralization of enamel subsurface lesions in the tooth. In view thereof, it was unexpected that a sugared confectionery composition could promote remineralization of tooth enamel. Some embodiments described herein provide at least about 12% more remineralization than comparable sugared confectionery compositions that are free of CPP-ACP and calcium and/or phosphate salts. Some embodiments provide at least about 18% more remineralization than such comparable confectionery compositions. In some embodiments, it has been found that the sugared confectionery compositions even promote a greater amount of remineralization of tooth enamel than sugar-free compositions that are substantially the same but free of CPP-ACP and calcium and/or phosphate salts.

The confectionery compositions also may include amounts of conventional additives as set forth above.

In some embodiments, the confectionery composition may include at least one flavor (flavorant, flavoring or flavor agent). The at least one flavor may include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Nonlimiting representative flavor oils include spearmint oil, cinnamon oil, oil of wintergreen (methyl salicylate), peppermint oil, Japanese mint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including lemon, orange, lime, grapefruit, yazu, sudachi, and fruit essences including apple, pear, peach, grape, blueberry, strawberry, raspberry, cherry, plum, pineapple, watermelon, apricot, banana, melon, apricot, ume, cherry, raspberry, blackberry, tropical fruit, mango, mangosteen, pomegranate, papaya and so forth. Other potential flavors whose release profiles can be managed include a milk flavor, a butter flavor, a cheese flavor, a cream flavor, and a yogurt flavor; a vanilla flavor; tea or coffee flavors, such as a green tea flavor, a oolong tea flavor, a tea flavor, a cocoa flavor, a chocolate flavor, and a coffee flavor; mint flavors, such as a peppermint flavor, a spearmint flavor, and a Japanese mint flavor; spicy flavors, such as an asafetida flavor, an ajowan flavor, an anise flavor, an angelica flavor, a fennel flavor, an allspice flavor, a cinnamon flavor, a camomile flavor, a mustard flavor, a cardamom flavor, a caraway flavor, a cumin flavor, a clove flavor, a pepper flavor, a coriander flavor, a sassafras flavor, a savory flavor, a Zanthoxyli Fructus flavor, a perilla flavor, a juniper berry flavor, a ginger flavor, a star anise flavor, a horseradish flavor, a thyme flavor, a tarragon flavor, a dill flavor, a capsicum flavor, a nutmeg flavor, a basil flavor, a marjoram flavor, a rosemary flavor, a bayleaf flavor, and a wasabi (Japanese horseradish) flavor; alcoholic flavors, such as a wine flavor, a whisky flavor, a brandy flavor, a rum flavor, a gin flavor, and a liqueur flavor; floral flavors; and vegetable flavors, such as an onion flavor, a garlic flavor, a cabbage flavor, a carrot flavor, a celery flavor, mushroom flavor, and a tomato flavor. These flavoring agents may be used in liquid or solid form and may be used individually or in admixture. Commonly used flavors include mints such as peppermint, menthol, spearmint, artificial vanilla, cinnamon derivatives, and various fruit flavors, whether employed individually or in admixture. Flavors may also provide breath freshening properties, particularly the mint flavors when used in combination with the cooling agents, described herein below.

In some embodiments, other flavorings include aldehydes and esters such as cinnamyl acetate, cinnamaldehyde, citral diethylacetal, dihydrocarvyl acetate, eugenyl formate, p-methylamisol, and so forth may be used. Generally any flavoring or food additive such as those described in Chemicals Used in Food Processing, publication 1274, pages 63-258, by the National Academy of Sciences, may be used. This publication is incorporated herein by reference. These may include natural as well as synthetic flavors.

Further examples of aldehyde flavorings include but are not limited to acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, .e., melonal (melon), 2,6-dimethyloctanal (green fruit), and 2-dodecenal (citrus, mandarin), cherry, grape, blueberry, blackberry, strawberry shortcake, and mixtures thereof.

In some embodiments, a flavoring agent may be employed in either liquid form and/or dried form. When employed in the latter form, suitable drying means such as spray drying the liquid may be used. Alternatively, the flavoring agent may be absorbed onto water soluble materials, such as cellulose, starch, sugar, maltodextrin, gum arabic and so forth or may be encapsulated. In still other embodiments, the flavoring agent may be adsorbed onto silicas, zeolites, and the like.

In some embodiments, the flavoring agents may be used in many distinct physical forms. Without being limited thereto, such physical forms include free forms, such as spray dried, powdered, beaded forms, encapsulated forms, and mixtures thereof.

In general, the at least one flavor is present in amounts of about 0.1% to about 15% by weight of the confectionery composition. More specifically, flavors may be present in amounts of about 0.5% to about 5.0% by weight of the confectionery compositions.

Coloring agents may be used in amounts effective to produce the desired color. The coloring agents may include pigments which may be incorporated in amounts up to about 6%, by weight of the confectionery composition. For example, titanium dioxide may be incorporated in amounts up to about 2%, and preferably less than about 1%, by weight of the composition. The colorants may also include natural food colors and dyes suitable for food, drug and cosmetic applications. These colorants are known as F.D.& C. dyes and lakes. The materials acceptable for the foregoing uses are preferably water-soluble. Illustrative nonlimiting examples include the indigoid dye known as F.D.& C. Blue No. 2, which is the disodium salt of 5,5-indigotindisulfonic acid. Similarly, the dye known as F.D.& C. Green No. 1 comprises a triphenylmethane dye and is the monosodium salt of 4-[4-(N-ethyl-p-sulfoniumbenzylamino) diphenylmethylene]-[1-(N-ethyl —N-p-sulfoniumbenzyl)-delta-2,5-cyclohexadieneimine]. A full recitation of all F.D.& C. colorants and their corresponding chemical structures may be found in the Kirk-Othmer Encyclopedia of Chemical Technology, 3rd Edition, in volume 5 at pages 857-884, which text is incorporated herein by reference.

A variety of well-known cooling agents may be employed. For example, among the useful cooling agents are included menthol, xylitol, erythritol, menthane, menthone, menthyl acetate, menthyl salicylate, N,2,3-trimethyl-2-isopropyl butanamide (WS-23), N-ethyl-p-menthane-3-carboxamide (WS-3), menthyl succinate, 3,1-menthoxypropane 1,2-diol and glutarate esters, among others, and combinations thereof. These and other suitable cooling agents are further described in the following U.S. patents, all of which are incorporated in their entirety by reference hereto: U.S. Pat. Nos. 4,230,688 and 4,032,661 to Rowsell et al.; U.S. Pat. No. 4,459,425 to Amano et al.; U.S. Pat. No. 4,136,163 to Watson et al.; and U.S. Pat. No. 5,266,592 to Grub et al. Warming agents may be selected from a wide variety of compounds known to provide the sensory signal of warming to the individual user. These compounds offer the perceived sensation of warmth, particularly in the oral cavity, and often enhance the perception of flavors, sweeteners and other organoleptic components. Useful warming agents include those having at least one allyl vinyl component, which may bind to oral receptors. Examples of suitable warming agents include, but are not limited to: vanillyl alcohol n-butylether (TK-1000, supplied by Takasago Perfumery Company Ltd., Tokyo, Japan); vanillyl alcohol n-propylether; vanillyl alcohol isopropylether; vanillyl alcohol isobutylether; vanillyl alcohol n-aminoether; vanillyl alcohol isoamylether; vanillyl alcohol n-hexylether; vanillyl alcohol methylether; vanillyl alcohol ethylether; gingerol; shogaol; paradol; zingerone; capsaicin; dihydrocapsaicin; nordihydrocapsaicin; homocapsaicin; homodihydrocapsaicin; ethanol; isopropyl alcohol; iso-amylalcohol; benzyl alcohol; glycerine; chloroform; eugenol; cinnamon oil; cinnamic aldehyde; phosphate derivatives thereof; and combinations thereof.

Tingling agents may be employed to provide a tingling, stinging or numbing sensation to the user. Tingling agents include, but are not limited to: Jambu Oleoresin or para cress (*Spilanthes* sp.), in which the active ingredient is Spilanthol; Japanese pepper extract (*Zanthoxylum peperitum*), including the ingredients known as Saanshool-I, Saanshool-II and Sanshoamide; black pepper extract (*piper nigrum*), including the active ingredients chavicine and piperine; Echinacea extract; Northern Prickly Ash extract; red pepper oleoresin; and effervescing agents, such as edible acids and bases, which may be encapsulated. Tingling agents are described in U.S. Pat. No. 6,780,443 to Nakatsu et al., U.S. Pat. No. 5,407,665 to McLaughlin et al., U.S. Pat. No. 6,159,509 to Johnson et al. and U.S. Pat. No. 5,545,424 to Nakatsu et al., each of which is incorporated by reference herein in its entirety.

Other conventional confectionery additives known to one having ordinary skill in the confectionery art also may be used in the compositions.

Some embodiments are directed to confectionery compositions including a solid portion and a dissolved portion of the solid portion. More specifically, upon consumption of a confectionery product, such as a hard candy, a portion of the solid hard candy begins to dissolve in the mouth of the individual. This dissolved portion of the solid portion forms in the oral cavity of the individual. Both the solid and dissolved portions of the confectionery product include a confectionery carrier, which may include at least one sweetener, CPP-ACP and a calcium and/or phosphate salt. Upon consumption, the confectionery compositions provide a greater amount of enamel subsurface remineralization in the tooth of a mammal than a confectionery composition which is substantially the same as the composition but which is free of CPP-ACP and calcium and/or phosphate salts. Additionally, the compositions may be free of added sodium bicarbonate.

Chewing Gum Compositions

Embodiments described herein provide chewing gum compositions including a gum base, a phosphopeptide or phosphoprotein stabilized calcium phosphate or calcium fluoride phosphate complex, such as CPP-ACP, which is an anticaries agent, and a calcium and/or phosphate salt. Some embodiments provide sugared chewing gum compositions, which include at least one sugar sweetener. The sugared chewing gum compositions also may include sugarless sweeteners in addition to the sugar sweeteners. Other embodiments provide sugar-free chewing gum compositions, which include only sugarless sweeteners. The chewing gum compositions promote remineralization of the tooth enamel to a greater extent than chewing gum compositions that are substantially the same but free of CPP-ACP and the calcium and/or phosphate salt.

Chewing gum compositions may be provided in a variety of different forms, such as, for example, slab, pellet, sticks, center-fill gums, deposited gums and compressed gums. The chewing gum compositions also may include at least one flavor and a variety of optional additives.

As described above, the chewing gum compositions may include a gum base. The gum base may include any component known in the chewing gum art. Such components may be water soluble, water-insoluble or a combination thereof. For example, the gum base may include elastomers, bulking agents, waxes, elastomer solvents, emulsifiers, plasticizers, fillers and mixtures thereof.

The elastomers (rubbers) employed in the gum base will vary greatly depending upon various factors such as the type of gum base desired, the consistency of gum composition desired and the other components used in the composition to make the final chewing gum product. The elastomer may be any water-insoluble polymer known in the art, and includes those gum polymers utilized for chewing gums and bubble gums. Illustrative examples of suitable polymers in gum bases include both natural and synthetic elastomers. For example, those polymers which are suitable in gum base compositions include, without limitation, natural substances (of vegetable origin) such as chicle, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, polyvinyl acetate and the like, and mixtures thereof.

The amount of elastomer employed in the gum base may vary depending upon various factors such as the type of gum base used, the consistency of the gum composition desired and the other components used in the composition to make the final chewing gum product. In general, the elastomer will be present in the gum base in an amount from about 10% to about 60% by weight, desirably from about 35% to about 40% by weight.

In some embodiments, the gum base may include wax. It softens the polymeric elastomer mixture and improves the elasticity of the gum base. When present, the waxes employed will have a melting point below about 60° C., and preferably between about 45° C. and about 55° C. The low melting wax may be a paraffin wax. The wax may be present in the gum base in an amount from about 6% to about 10%, and preferably from about 7% to about 9.5%, by weight of the gum base.

In addition to the low melting point waxes, waxes having a higher melting point may be used in the gum base in amounts up to about 5%, by weight of the gum base. Such high melting waxes include beeswax, vegetable wax, candelilla wax, carnuba wax, most petroleum waxes, and the like, and mixtures thereof.

In addition to the components set out above, the gum base may include a variety of other ingredients, such as components selected from elastomer solvents, emulsifiers, plasticizers, fillers, and mixtures thereof.

The gum base may contain elastomer solvents to aid in softening the elastomer component. Such elastomer solvents may include those elastomer solvents known in the art, for example, terpinene resins such as polymers of alpha-pinene or beta-pinene, methyl, glycerol and pentaerythritol esters of rosins and modified rosins and gums such as hydrogenated, dimerized and polymerized rosins, and mixtures thereof. Examples of elastomer solvents suitable for use herein may include the pentaerythritol ester of partially hydrogenated wood and gum rosin, the pentaerythritol ester of wood and gum rosin, the glycerol ester of wood rosin, the glycerol ester of partially dimerized wood and gum rosin, the glycerol ester of polymerized wood and gum rosin, the glycerol ester of tall oil rosin, the glycerol ester of wood and gum rosin and the partially hydrogenated wood and gum rosin and the partially hydrogenated methyl ester of wood and rosin, and the like, and mixtures thereof. The elastomer solvent may be employed in the gum base in amounts from about 2% to about 15%, and preferably from about 7% to about 11%, by weight of the gum base.

The gum base may also include emulsifiers which aid in dispersing the immiscible components into a single stable system. The emulsifiers useful in this invention include glyceryl monostearate, lecithin, fatty acid monoglycerides, diglycerides, propylene glycol monostearate, and the like, and mixtures thereof. The emulsifier may be employed in amounts from about 2% to about 15%, and more specifically, from about 7% to about 11%, by weight of the gum base.

The gum base may also include plasticizers or softeners to provide a variety of desirable textures and consistency properties. Because of the low molecular weight of these ingredients, the plasticizers and softeners are able to penetrate the fundamental structure of the gum base making it plastic and less viscous. Useful plasticizers and softeners include lanolin, palmitic acid, oleic acid, stearic acid, sodium stearate, potassium stearate, glyceryl triacetate, glyceryl lecithin, glyceryl monostearate, propylene glycol monostearate, acetylated monoglyceride, glycerine, and the like, and mixtures thereof. Waxes, for example, natural and synthetic waxes, hydrogenated vegetable oils, petroleum waxes such as polyurethane waxes, polyethylene waxes, paraffin waxes, microcrystalline waxes, fatty waxes, sorbitan monostearate, tallow, propylene glycol, mixtures thereof, and the like, may also be incorporated into the gum base. The plasticizers and softeners are generally employed in the gum base in amounts up to about 20% by weight of the gum base, and more specifically in amounts from about 9% to about 17%, by weight of the gum base.

Plasticizers also include hydrogenated vegetable oils, such as soybean oil and cottonseed oils, which may be employed alone or in combination. These plasticizers provide the gum base with good texture and soft chew characteristics. These plasticizers and softeners are generally employed in amounts from about 5% to about 14%, and more specifically in amounts from about 5% to about 13.5%, by weight of the gum base.

Anhydrous glycerin may also be employed as a softening agent, such as the commercially available United States Pharmacopeia (USP) grade. Glycerin is a syrupy liquid with a sweet warm taste and has a sweetness of about 60% of that of cane sugar. Because glycerin is hygroscopic, the anhydrous glycerin may be maintained under anhydrous conditions throughout the preparation of the chewing gum composition.

In some embodiments, the gum base may also include effective amounts of bulking agents such as mineral adjuvants which may serve as fillers and textural agents. Useful mineral adjuvants include calcium carbonate, magnesium carbonate, alumina, aluminum hydroxide, aluminum silicate, talc, tricalcium phosphate, dicalcium phosphate, calcium sulfate and the like, and mixtures thereof. These fillers or adjuvants may be used in the gum base compositions in various amounts. Preferably the amount of filler, when used, will be present in an amount from about 15% to about 40%, and desirably from about 20% to about 30%, by weight of the gum base.

A variety of traditional ingredients may be optionally included in the gum base in effective amounts such as flavor agents and coloring agents, antioxidants, preservatives, and the like. For example, titanium dioxide and other dyes suitable for food, drug and cosmetic applications, known as F. D. & C. dyes, may be utilized. An anti-oxidant such as butylated hydroxytoluene (BHT), butylated hydroxyanisole (BHA), propyl gallate, vitamin E and mixtures thereof, may also be included. Other conventional chewing gum additives known to one having ordinary skill in the chewing gum art may also be used in the gum base.

In general, the gum base is present in amounts of about 5% to about 95% by weight of the chewing gum composition. More specifically, the gum base may be present in amounts of about 20% to about 60% by weight of the chewing gum composition.

Chewing gum products may be prepared using standard techniques and equipment known to those skilled in the art. The apparatus useful in accordance with the embodiments described herein includes mixing and heating apparatus well known in the chewing gum manufacturing arts, and therefore the selection of the specific apparatus will be apparent to the artisan. For general chewing gum preparation processes see U.S. Pat. No. 4,271,197 to Hopkins et al, U.S. Pat. No. 4,352,822 to Cherukuri et al and U.S. Pat. No. 4,497,832 to Cherukuri et al, each of which is incorporated herein by reference in its entirety.

In compressed gum formats, the gum base may be in a particulate form, such as, but not limited to, a powdered or granular gum base, as opposed to molten or thermoplastic gum base. The particulate gum base may be essentially free of water and can readily be formed into any desired shape, such as by compression.

The particulate gum base may be formed using standard grinding techniques known in the art. The starting material may be any conventional gum base, such as those used to produce molten gum bases. The particulate gum base may be formed, for example, by shredding, grinding or crushing the gum base or other processes, as described in U.S. Pat. Nos. 3,262,784, 4,405,647, 4,753,805 and 6,290,985 and U.S. Publication No. 2003/00276871, all of which are incorporated herein by reference in their entirety.

Desirably, the particulate gum base is ground or the like into a particulate form that is similar in particle size to the tableting powder. By using components of like particle size, a homogenous mix of gum base and tableting powder may be achieved, which may provide a gum tablet of similar homogenous make-up. The gum base and tableting powder may have a particle size of about 4 to about 100 mesh, desirably about 8 to about 25 mesh, and more desirably about 12 to about 20 mesh.

The particulate gum base may be present in amounts of about 10% to about 80% by weight of the chewing gum composition, or tablet, desirably about 20% to about 50% by weight, and more desirably about 30% to about 40% by weight.

The particulate gum base may be combined with a tableting powder to form the pressed gum tablet. The tableting powder can be in a dry, finely-divided form. Desirable particle size is provided above. The tableting powder may be a sucrose-based, dextrose-based or polyol-based powder, or combinations thereof. For example, the polyol-based powder may be a sorbitol or mannitol powder. The tableting powder may include other optional ingredients, such as flavor agents, color agents, sugar and/or sugarless sweeteners, and the like and combinations thereof.

In some embodiments, it may be desirable to combine a food-grade lubricant with the particulate gum base and tableting powder. Food-grade lubricants may assist in processing the gum composition into pressed tablets. More specifically, lubricants are used to prevent excess wear on dies and punches in tableting manufacture. Lubricants may be useful immediately after compression of the tablet within the die to reduce friction between the tablet and inner die wall.

The food-grade lubricant may be added separately or it may be included with the tableting powder, as in some commercially available tableting powders. Examples of suitable food-grade lubricants include: metallic stearates; fatty acids; hydrogenated vegetable oil; partially hydrogenated vegetable oils; animal fats; polyethylene glycols; polyoxyethylene monostearate; talc; silicon dioxide; and combinations thereof. Food-grade lubricants may be present in amounts of about 0-6% by weight of the gum composition.

Alternatively, in some embodiments, a compressible chewing gum composition can be formed by preparing a chewing gum composition and then grinding the mixture. The chewing gum composition can be prepared by mixing together molten gum base, bulk sweeteners, softeners, plasticizers, other sweeteners, colors, and the like by any known mixing technique such as dough mixing. As with preparation of the particulate gum base, the chewing gum mixture can be formed into a particulate chewing gum composition using standard grinding techniques known in the art. The particulate chewing gum may be formed, for example, by shredding, grinding or crushing the chewing gum or other processes, as described in U.S. Pat. Nos. 3,262,784, 4,405,647, 4,753,805 and 6,290,985 and U.S. Publication No. 2003/00276871, all of which are incorporated herein by reference in their entirety.

As described above, the compressible chewing gum composition can be in the form of a pressed gum tablet. In some embodiments, the particulate gum base and modified release ingredients are pressed into a tablet form. Upon chewing, the pressed gum tablet consolidates into a soft chewy substance.

In some embodiments, the compressible chewing gum composition is a single-layer pressed tablet. In some embodiments, the compressible chewing gum composition is a multi-layer pressed tablet. Multi-layer tablet embodiments may have any desirable number of layers. Different layers may have the same or different thicknesses. In addition, different layers may include the same or different ingredients.

The pressed gum tablet also may have a coating layer surrounding the tablet. The coating layer may contain any ingredients conventionally used in the chewing gum art. For instance, the coating may contain sugar, polyols or high intensity sweeteners or the like, coloring agents, flavor agents and warming and/or cooling agents, among others.

The compressible chewing gum compositions, or pressed tablets, desirably have a very low moisture content. In some embodiments, the tablets are essentially free of water. Accordingly, some embodiments have a total water content of greater than about 0% to about 5% by weight of the composition. The density of the composition, or tablet, may be about 0.2 to about 0.8 g/cc. Further, the compressible chewing gum compositions, or tablets, may have a dissolution rate of about 1 to about 20 minutes. When in a pressed tablet form, the chewing gum may have a Shore hardness of about 30 to about 200.

In contrast to dough mixed chewing gums where the gum mixture can achieve temperatures of 35° C. to 60° C., compressed chewing gum temperatures can remain around ambient temperature (23° C. to 25° C.). In some embodiments, subjecting the compressible chewing gum compositions to lower temperatures can protect temperature sensitive ingredients from thermal degradation. Similarly, the absence of intimate mixing at temperatures above ambient can protect delivery systems that include temperature sensitive ingredients or ingredients subject to degradation from gum ingredients such as flavors, plasticizers, etc. Thus, ingredients susceptible to thermal or chemical degradation due to conventional dough mixing can be less likely to experience degradation in compressed chewing gum systems.

The chewing gum compositions also may include any of the sweeteners and optional additives set forth above for the confectionery compositions. Sweeteners, CPP-ACP and calcium and/or phosphate salts may be included in the chewing gum compositions in the same amounts and forms as described above. For example, the CPP-ACP may be encapsulated, unencapsulated or a mixture of both forms. The chewing gum product formed from the chewing gum compositions may contain, for instance, about 1 mg CPP-ACP, more specifically about 1.5 mg, may be encapsulated, in some embodiments. Similar to above, such chewing gum compositions provide a greater amount of tooth enamel remineralization than chewing gum compositions that are substantially the same as the compositions provided by such embodiments but free of CPP-ACP and calcium and/or phosphate salts. For instance, in some embodiments, sugared chewing gum compositions provide at least about 2.8% enamel subsurface remineralization, and in some embodiments, at least about 8% enamel subsurface remineralization.

Any of the optional additives described above also may be included in the chewing gum compositions, as well as any conventional chewing gum additives known to those skilled in the art.

Some embodiments are directed to chewing gum compositions including a solid portion and a dissolved portion of the solid portion. More specifically, upon consumption of a chewing gum product, a portion of the solid chewing gum product dissolves in the mouth of the of the individual. The solid portion of the chewing gum product includes a gum base, CPP-ACP and a calcium and/or phosphate salt. The dissolved portion includes CPP-ACP and a calcium and/or phosphate salt. Both the solid and dissolved portions may include at least one sweetener, such as a sugar sweetener in sugared chewing gum embodiments. Upon consumption, the chewing gum compositions provide a greater amount of enamel subsurface remineralization in the tooth of a mammal than a chewing gum composition which is substantially the same as the composition but which is free of CPP-ACP and calcium and/or phosphate salts. Additionally, the compositions may be free of added sodium bicarbonate.

As mentioned above, the chewing gum compositions may be provided as a variety of different products, such as, slab, pellet, sticks, center-fill gums, deposited gums and compressed gums.

Any of the chewing gum or confectionery products described herein may have a coating thereon, which may at least partially surround or enrobe the product.

More specifically, in some embodiments, the chewing gum or confectionery product may include a chewing gum or confectionery region and a coating region. The chewing gum region may be formed from any of the chewing gum compositions described above. Similarly, the confectionery region may be formed from any of the confectionery compositions described above. The coating region may at least partially surround the chewing gum or confectionery region. CPP-ACP may be located in the chewing gum or confectionery region, in the coating region or in both regions. Similarly, calcium and/or phosphate salts may be located in the chewing gum or confectionery region, in the coating region or in both regions.

Some other embodiments are directed to center-fill chewing gum or confectionery products. Center-fill chewing gums may include a center-fill region and a gum region at least partially surrounding or positioned adjacent to the center-fill region. The gum region may be formed from any of the chewing gum compositions described above. Center-fill confectioneries, such as, for example, center-fill candy, may include a center-fill region and a confectionery region, such as a hard or chewy candy region, at least partially surrounding or positioned adjacent to the center-fill region. The confectionery region may be formed from any of the confectionery compositions described above. CPP-ACP may be located in the gum or confectionery region, the center-fill region or in both regions. CPP-ACP may be encapsulated and/or unencapsulated in any of these regions. Similarly, calcium and/or phosphate salts may be located in the gum or confectionery region, the center-fill region or in both regions.

The center-fill region of the gum or confectionery product may be a liquid, solid or semi-solid, gas, or the like. Embodiments that include a liquid center-fill composition, as well as some semi-solid center-fill compositions, may involve concerns regarding retention of the liquid center during manufacturing and shelf-life, as mentioned above. In chewing gum embodiments, it may be desirable, therefore, to employ gum region compositions with liquid-fill gums that substantially reduce or prevent leaking of the liquid center. Suitable gum region compositions are discussed in assignee's co-pending U.S. application Ser. No. 11/210,954, which is incorporated by reference herein in its entirety.

In some embodiments, center-fill products also may include a coating region, which at least partially surrounds the gum or confectionery region.

In coated chewing gum and confectionery embodiments, the outer coating may be soft, hard or crunchy. Any suitable coating materials known to those skilled in the art may be employed. Typically, the outer coating may include sorbitol, maltitol, xylitol, isomalt, erythritol and other crystallizable polyols; sucrose may also be used. Furthermore the coating may include several opaque layers, such that the chewing gum or confectionery composition is not visible through the coating itself, which can optionally be covered with a further one or more transparent layers for aesthetic, textural and protective purposes. The outer coating may also contain small amounts of water and gum arabic. The coating can be further coated with wax. The coating may be applied in a conventional manner by successive applications of a coating solution, with drying in between each coat. As the coating dries it usually becomes opaque and is usually white, though other colorants may be added. A polyol coating can be further coated with wax. The coating can further include colored flakes or speckles. If the composition includes a coating, it is possible that one or more oral care actives can be dispersed throughout the coating. This is especially preferred if one or more oral care actives is incompatible in a single phase composition with another of the actives. Flavors may also be added to yield unique product characteristics.

Other materials may be added to the coating to achieve desired properties. These materials may include without limitations, cellulosics such as carboxymethyl cellulose, gelatin, xanthan gum and gum arabic.

The coating composition may be applied by any method known in the art including the method described above. The coating composition may be present in an amount from about 2% to about 60%, more specifically from about 25% to about 45% by weight of the total chewing gum or confectionery product.

Center-fill products may be formed by any technique known in the art, which includes the method described by U.S. Pat. No. 6,280,780 to Degady et al. ("Degady"), which is incorporated by reference herein in its entirety.

Soft Confectionery Compositions

In some embodiments, the oral delivery systems may be in the form of various soft confectionery formats. Soft confectionery formats may include, but are not limited to, nougat, caramel, taffy, gummies and jellies. Such delivery systems also may include any of the optional additives described above.

Soft confectionery compositions may include a confectionery base and a variety of optional additives, such as any of the additives set forth above. Upon consumption, the phosphopeptide or phosphoprotein stabilized calcium phosphate or calcium fluoride phosphate complex and calcium and/or phosphate salt releases from the soft confection and provides the remineralization benefits discussed above.

Some soft confectionery compositions include nougat compositions, which may include two principal components, a high-boiled candy and a frappe. By way of example, egg albumen or substitute thereof is combined with water and whisked to form a light foam. Sugar and glucose are added to water and boiled typically at temperatures of from about 130° C. to 140° C. and the resulting boiled product is poured into a mixing machine and beaten until creamy. The beaten albumen and flavoring agent are combined with the creamy product and the combination is thereafter thoroughly mixed.

In some embodiments, a caramel composition may include sugar (or sugar substitute), corn syrup (or polyol syrup), partially hydrogenated fat, milk solids, water, butter, flavors, emulsifiers, and salt. To prepare the caramel, the sugar/sugar substitute, corn syrup/polyol syrup, and water may be mixed together and dissolved over heat. Then, the milk solids may be mixed in to the mass to form a homogeneous mixture. Next, the minor ingredients may be mixed in with low heat. The heat then may be increased to boiling. Once sufficient water is removed and color/flavor developed, the mass may be cooled somewhat and temperature sensitive ingredients may be mixed in prior to discharging and forming/shaping/wrapping the finished product.

In some embodiments, a taffy composition may include sugar (or sugar substitute), corn syrup (or polyol syrup), partially hydrogenated fat, water, flavors, emulsifiers, and salt. The process for preparing taffy can be similar to that for caramel and, optionally, the final taffy mass may be pulled to develop its desired texture.

In some embodiments, a gummi composition may include sugar (or sugar substitute), corn syrup (or polyol syrup), gelatin (or suitable hydrocolloid), flavor, color, and optionally acid. The gummi may be prepared by hydrating the gelatin or suitable hydrocolloid, heating the sugar/corn syrup (sugar substitute/polyol syrup) and combining the two components with heat. Once the combined mixture reaches its final temperature or suitable sugar solids level, components such as flavor, color, and the like may be incorporated into the mixture and then poured into molds prior to cooling, wrapping, and finishing. Various surface treatments such as applications of wax or fat can be applied to decrease sticking.

In some embodiments, a jelly composition may include a starch-based jelly or a pectin-based jelly. As with gummis, jelly products may be produced by hydrating the hydrocolloid and combining the hydrated mixture with a cooked syrup component. The mixture then may be cooked to a final moisture content and minor components may be incorporated. As with gummis, jelly candies may be poured into molds such as starch molds. As with gummis, surface treatments, such as fats or waxes, may be applied. Additionally, jelly candies may have dry surface treatments, such as applications of sanding sugar, acid, non-pareils, and the like.

Additionally, in some embodiments, various soft confectionery configurations with multiple regions may be employed. These configurations may include, but are not limited to, liquid center-fill, powder center-fill, hard coated, soft coated, laminated, layered and enrobed. In some embodiments, the phosphopeptide or phosphoprotein stabilized calcium phosphate or calcium fluoride phosphate complex and calcium and/or phosphate salt may be included in one region or in multiple regions of the product.

Chocolate Confectionery Compositions

The oral delivery systems also can be in the form of various chocolate confectionery formats. Chocolate confectioneries can include milk chocolate, dark chocolate, and/or white chocolate. Milk chocolate can include milk solids with other milk chocolate ingredients such as cocoa liquor, cocoa butter and/or other fats, sweeteners, emulsifiers, flavors, and the like. In some embodiments, the milk solids can be in an amount of 5% by weight of the milk chocolate composition to amounts of greater than 40% by weight of the milk chocolate composition. The milk solids can be in the form of dry milk powder or liquid milk.

Dark chocolate can include ingredients as in milk chocolate but may have little to no milk solids components. White chocolate can include ingredients such as fats, sweeteners, flavors, emulsifiers, and the like but does not contain cocoa liquor. White chocolate is also referred to as compound coating.

Suitable methods for combining chocolate ingredients are well known to those skilled in the art, and include for example a food grade blender, a mixer, and the like.

Chocolate delivery systems also may include any of the optional additives described above.

Gels, Dentifrices and Toothpastes

Some embodiments are directed to oral delivery systems in the form of a gel, dentifrice or toothpaste for delivery of the phosphopeptide or phosphoprotein stabilized calcium phosphate or calcium fluoride phosphate complex and calcium and/or phosphate salt. Such delivery systems also may include any of the optional additives described above.

Remineralizing gels typically include a non-toxic gelling compound as are conventionally used in foods, including but not limited to agar, gelatine, carboxymethyl cellulose, chitin, gum acacia, gum arabic, gum xanthum, hydroxyethyl cellulose and hydroxypropyl methylcellulose. The gels can be formulated to have a neutral pH to avoid irritation of oral tissues upon prolonged exposure. Each gel also may include sufficient water or other aqueous solution to produce the desired consistency, as well as high molecular weight crystal growth inhibitors, and any o the optional additives described above, such as flavoring and coloring agents. High molecular weight crystal growth inhibiting agents include the gelling agents themselves, as described above, and also phosphoproteins (such as are disclosed in Termine & Conn, 1976, Calcif. Tiss. Res. 2: 149-157), polycarboxylates (such as are disclosed in Howie-Meyers et al., 1995, in Mineral Scale Formation and Inhibition, Amjad, ed., Plenum Press: New York, Ch. 15, pp. 169-182), and polyphosphorylated polyvinyl alcohol (as are described in Shimabayashi et al., 1995, in Mineral Scale Formation and Inhibition, Amjad, ed., Plenum Press: New York, Ch. 14, pp. 157-168).

Gels may be provided as a dry powder including the complex and calcium and/or phosphate salts and any other optional additives. In such embodiments, the gel is reconstituted by adding water or other liquid containing advantageous additives (such as colorings, flavorings, sweeteners, gelling agents, and the like).

Dentifrices and toothpastes contain conventional components of dentifrices and toothpastes, including but not limited to sweeteners such as sorbitol or saccharine, abrasives such as hydrated silica, foaming agents such as sodium lauryl sulfate, binders such as various forms of cellulose or gums, lubricants such as glycerin, pigment whiteners such as titanium oxide, food coloring and water.

As with gels, dentifrices and toothpastes are advantageously provided as a dry powder including the complex and calcium and/or phosphate salt and any optional additives, such as dry flavorings, sweeteners, gelling agents, and other components are described above. In such embodiments, the dentifrice or toothpaste is reconstituted by adding water or other liquid including advantageous additives (such as colorings, flavorings, sweeteners, gelling agents, and the like).

An additive of particular significance in dental applications is fluoride containing compounds. In toothpaste and gel embodiments, for example, fluoride salts such as NaF, $CaF_2$, SnF2, $Na_2 PO_3 F$ or $Na_2 SiF_6$ may be added in sufficient quantity to increase the rate of formation of HA and fluorapatite. Some embodiments may have a fluoride content of about 200 to 2200 ppm. The total amount of fluoride released during use of the toothpastes and gels may be 0.05 to 10 mg.

Mouthwashes, Rinses and Sprays

The oral delivery system may be a mouthwash, rinse or spray in some embodiments. Components of mouthwashes, rinses and sprays typically include water being present in an amount of from about 45% to 95% by weight of the composition, and one or more of ethanol up to 70% by weight of the composition, a humectant up to 50% by weight of the composition, a surfactant from about 0.01% to 7% by weight of the composition, a flavoring agent from about 0.04% to 2% by weight of the composition, a sweetening agent from about 0.1% to 3% by weight of the composition, and a coloring agent from about 0.001% to 0.5% by weight of the composition. Mouthwashes, rinses and sprays also typically include one or more of an anticaries agent from about 0.05% to 0.3% by weight of the composition (e.g., fluoride ion), and an anticalculus agent from about 0.1% to 3% by weight of the composition. Any of the optional additives set forth above also may be included.

Beverages

Some embodiments are directed to oral delivery systems in the form of a beverage for delivery of the phosphopeptide or phosphoprotein stabilized calcium phosphate or calcium fluoride phosphate complex and calcium and/or phosphate salt. A variety of different beverage compositions may be employed. Examples of suitable beverages are provided below. Such beverage compositions also may include any of the optional additives described above.

Juice-Based Compositions

Juice-based compositions generally contain a juice component obtained from fruit or vegetable. The juice component can be used in any form such as a juice form, a concentrate, an extract, a powder, or the like.

Suitable juices include, for example, citrus juice, non-citrus juice, or mixtures thereof, which are known for use in beverages. Examples of such juices include, non-citrus juices such as apple juice, grape juice, pear juice, nectarine juice, currant juice, raspberry juice, gooseberry juice, blackberry juice, blueberry juice, strawberry juice, custard-apple juice, pomegranate juice, guava juice, kiwi juice, mango juice, papaya juice, watermelon juice, cantaloupe juice, cherry juice, cranberry juice, peach juice, apricot juice, plum juice, and pineapple juice; citrus juices such as orange juice, lemon juice, lime juice, grapefruit juice, and tangerine juice; and vegetable juice such as carrot juice and tomato juice; or a combination comprising at least one of the foregoing juices.

Unless otherwise indicated, juice as used can include fruit or vegetable liquids containing a percentage of solids derived from the fruit or vegetable, for example pulp, seeds, skins, fibers, and the like, and pectin, which is naturally occurring in the fruit or vegetable. The amount of solids in the juice can be about 1 to about 75 wt %, specifically about 5 to about 60 wt %, more specifically about 10 to about 45 wt %, and yet more specifically about 15 to about 30 wt % each based on the total weight of the juice. Higher concentrations of solids can be found in juice concentrates, purees, and the like.

The amount of juice component present in the juice-based composition generally can be about 0.1 wt % to about 95 wt % based on the total weight of the composition, specifically about 5 wt % to about 75 wt %, and more specifically about 10 wt % to about 50 wt % each based on the total weight of the composition. Amounts may vary depending upon whether the composition is a concentrate or a ready to drink beverage, for example. The remaining components in the juice-based composition can be added water or other suitable liquid, a sweetening agent, a flavoring agent, or other additives as described herein.

The juice-based composition can be non-carbonated or carbonated.

In one embodiment, the juice-based composition is fortified with solubilized calcium in the form of calcium carbonate, calcium oxide, or calcium hydroxide, for example. A food-grade acid is added to the calcium fortified juice-based composition to improve the solubility of calcium. Exemplary food-grade acids suitable for use in the juice-based composition are further discussed herein, specifically citric acid, malic acid, or a combination comprising at least one of the foregoing food-grade acids.

In some embodiments, the juice-based composition can be formed from a fruit or vegetable using a hot break or cold break process. In both processes, the fruit or vegetable is macerated and passed through conventional equipment to separate out seeds, skins and other undesired solids. The composition is then concentrated by conventional techniques. In hot break processes, the fruit or vegetable is typically heated during maceration or immediately thereafter to deactivate enzymes that may degrade the product and decrease the viscosity of the product. In cold break processes, the fruit or vegetable typically are processed at lower temperatures than hot break. A hot break process accordingly may provide a thicker product than those produced by a cold break process.

In one embodiment, the juice-based composition is pasteurized to destroy unwanted microorganisms. Suitable pasteurization conditions of juice-based compositions can be selected by one of ordinary skill in the art without undue experimentation using the guidelines provided. An exemplary pasteurization process to sterilize the juice-based composition is by heating the composition to about 60 to about 80° C. for about 6 to about 15 minutes in an aseptic environment.

In another embodiment, the juice-based composition is filled into a beverage container and then subjected to pasteurization conditions. Alternatively, the composition is hot-filled into a beverage container at temperatures sufficient to sterilize the composition in the container.

In another embodiment, the juice-based composition can contain a preservative allowing the composition to be cold-filled into a beverage container without the need for pasteurization. Specifically, the preservatives can be added to lower the pH level of the beverage to pH of about 3 to about 4.5. Suitable preservatives are discussed in detail herein.

Milk-Based Compositions

Milk-based compositions generally contain a dairy component which can contain varying amounts of milk proteins (e.g., casein, whey protein, and the like), fats, lactose, and water. Exemplary dairy components include yogurt, cream, whole milk, low or reduced fat milk, skim milk, milk solids, condensed milk, or a combination comprising at least one of the foregoing dairy components.

In some embodiments, non-dairy components may replace part or all of the dairy components in the milk-based composition. Suitable non-dairy components include soy milk, almond milk, coconut milk, rice milk, and the like, or a combination comprising at least one of the foregoing.

Stabilizers can be added to the milk-based composition to prevent precipitation. Exemplary stabilizers include hydrocolloids such as pectin, propylene glycol alginate, and the like, as well as the stabilizers described further herein.

The amount of milk proteins in a milk-based beverage composition can be about 0.1% to about 10% by weight based on the total weight of the milk-based beverage composition, specifically about 0.5% to about 5% by weight, and more specifically about 1.0% to about 4% by weight.

The milk-based composition can contain a sweetening agent, coloring agent, or other additives as disclosed herein. The milk-based composition can be non-carbonated or carbonated.

In some embodiments, the milk-based beverage is lactose free.

The process for preparing milk-based beverage compositions generally includes mixing and emulsifying a dairy component or non-dairy component with an emulsifier to form an emulsified component. The emulsified component can be pasteurized, cooled, and blended with a second component, which can contain a flavoring agent, a sweetening agent, other additives, or water or other suitable liquid to form a beverage composition. The blending can be performed under aseptic conditions to ensure product integrity.

Suitable conditions for the pasteurization of milk-base compositions can be selected by one of ordinary skill in the art without undue experimentation using the guidelines provided. An exemplary pasteurization process to sterilize the emulsified component or other dairy component can be effected at temperatures of about 130 to about 140° C. for about 30 seconds to about 2 minutes in an aseptic environment. Alternatively, the pasteurization can be performed at about 115 to about 125° C. for about 20 to about 30 minutes in an aseptic environment.

In another embodiment, the milk-based composition is filled into a beverage container and then subjected to the pasteurization conditions.

Alcoholic Compositions

The compositions described herein may further comprise an alcoholic composition. Examples of suitable alcoholic compositions include beer, spirit, liqueur, wine, or a combination comprising at least one of the foregoing. In some embodiments, the level of alcohol, as measured by the amount of ethanol contained in the beverage composition can be about 0.5 vol % to about 20 vol % based on the total volume of the beverage composition.

Carbonated Compositions

A carbonated beverage composition typically contains about 0.1 to about 5.0 volumes of gas or gasses, typically carbon dioxide, per volume of the beverage composition. The carbonation can be effected by forceful introduction of the gas under pressure to the beverage composition. Cooling the beverage composition allows for greater amounts of carbon dioxide to be solubilized by the beverage composition. Carbonation can be used to enhancing the flavor, sweetness, taste, and mouth-feel of the composition. Additionally, carbonation lowers the pH of the composition.

In one embodiment, the carbonation can be added to the finished, noncarbonated beverage composition, which contains all of the desired beverage components.

In another embodiment, the carbonation is added to a desired volume of water to form a carbonated water. The carbonated water can then be combined with a composition such as a beverage concentrate or beverage syrup to produce the finished carbonated beverage composition.

Once the carbonated beverage composition has been prepared, the carbonated beverage composition can be packaged in containers and sealed using methods, packaging, and equipment selected by those of ordinary skill in the art without undue experimentation.

In some embodiments, carbonation can be added at the point of consumption. For example, in a restaurant or convenience store, a fountain beverage consisting of a beverage syrup and a source of carbonation is prepared for imminent consumer consumption.

Frozen Compositions

A "frozen beverage composition" as used herein includes a beverage composition having ice crystals suspended therein to provide a viscous, yet drinkable beverage. The consistency of the frozen beverage composition allows it to have a "slushy" or "spoonable" consistency. The ice crystals can be present in the frozen beverage composition in an amount of about 20 to about 90 wt %, specifically about 30 to about 70 wt %, and yet more specifically about 40 to about 50 wt % ice solids each based on the total weight of the frozen beverage composition.

Due to the lower temperature of the frozen beverage composition compared with other beverages, choice in the amount of flavoring agent and/or sweetening agent can be different. Suitable amounts of flavoring agent and sweetening agent can be selected by one of ordinary skill in the art without undue experimentation.

The frozen beverage composition can contain a buffering salt, which aids in lowering the freezing point of the beverage composition and to maintain the "slushy" texture. Suitable buffering salts include sodium, potassium, and calcium salts of citric acid or phosphoric acid: sodium citrate, potassium citrate, disodium phosphate, dipotassium phosphate, monocalcium phosphate, tricalcium phosphate, or a combination comprising at least one of the foregoing buffering salts.

Gel Compositions

A "gel beverage composition" as used herein includes a beverage composition having a thickening agent to provide a viscous, yet drinkable beverage. The consistency of the gel beverage composition allows it to have a "semi-solid" or "spoonable" consistency. Thickening agents (sometimes referred to as hydrocollids) can include, but are not limited to natural and synthetic gums, for example locust bean gum, guar gum, gellan gum, xanthan gum, gum ghatti, modified gum ghatti, tragacanth gum, carrageenan, and the like; natural and modified starches, for example pregelatinized starch (corn, wheat, tapioca), pregelatinized high amylose-content starch, pregelatinized hydrolyzed starches (maltodextrins, corn syrup solids), chemically modified starches such as pregelatinized substituted starches (e.g., octenyl succinate), and the like; cellulose derivatives, for example carboxymethylcellulose, sodium carboxymethylcellulose, and the like; polydextrose; whey or whey protein concentrate; pectin; gelatin; or a combination comprising at least one of the foregoing thickening agents.

Due to the textural difference of the gel beverage composition compared with other beverages, choice in the amount of flavoring agent and/or sweetening agent can be different. Suitable amounts of flavoring agent and sweetening agent can be selected by one of ordinary skill in the art without undue experimentation.

Any of the beverage compositions described herein may include flavors and sweeteners, as described above, and a variety of optional additives. For instance, in some embodiments, the beverage composition may include additive sweeteners, such as Lo han guo, stevia, monatin, or the like, or combinations thereof. In some embodiments, the composition may include optional additives such as antioxidants, amino acids, caffeine, coloring agents ("colorants", "colorings"), emulsifiers, flavor potentiators, food-grade acids, minerals, micronutrients, plant extracts, phytochemicals ("phytonutrients"), preservatives, salts including buffering salts, stabilizers, thickening agents, medicaments, vitamins, or a combination comprising at least one of the foregoing additives. Those of ordinary skill in the art will appreciate that certain additives may meet the definition or function according to more than one of the above-listed additive categories.

Suitable salts for use in the composition include, alkali or alkaline earth metal chlorides, glutamates, and the like. For example, monosodium glutamate, potassium chloride, sodium chloride, or a combination comprising at least one of the foregoing salts. The salts can be added to the beverage as a flavor potentiator as previously described.

Suitable food-grade acids for use in the composition include, for example, acetic acid, adipic acid, ascorbic acid, butyric acid, citric acid, formic acid, fumaric acid, glyconic acid, lactic acid, malic acid, phosphoric acid, oxalic acid, succinic acid, tartaric acid, or a combination comprising at least one of the foregoing food-grade acids. The food-grade acid can be added as acidulant to control the pH of the beverage and also to provide some preservative properties; or to stabilize the beverage.

The pH of the beverage may also be modified by the addition of food-grade compounds such as ammonium hydroxide, sodium carbonate, potassium carbonate, sodium bicarbonate, and the like, or a combination comprising at least one of the foregoing. Additionally, the pH of the beverage can be adjusted by the addition of carbon dioxide.

In some embodiments, the tartness of the beverage may be varied by selecting and combining acids to provide a desired tartness perception. Some factors to consider in determining a desired tartness include, but are not limited to, the acid's dissociation constant, solubility, pH, etc. These variables can be measured by measuring the titratable acidity of the beverage composition.

Coloring agents can be used in amounts effective to produce a desired color for the composition. The colorants may include pigments, natural food colors and dyes suitable for food, drug and cosmetic applications. A full recitation of all F.D.& C. colorants and their corresponding chemical structures can be found in the Kirk-Othmer Encyclopedia of Chemical Technology, 3rd Edition, in volume 5 at pages 857-884, of which text is incorporated herein by reference.

As classified by the United States Food, Drug, and Cosmetic Act (21 C.F.R. 73), colors can include exempt from certification colors (sometimes referred to as natural even though they can be synthetically manufactured) and certified colors (sometimes referred to as artificial), or a combination comprising at least one of the foregoing. In some embodiments, exemplary exempt from certification or natural colors can include, annatto extract, (E160b), bixin, norbixin, astaxanthin, dehydrated beets (beet powder), beetroot red/betanin (E162), ultramarine blue, canthaxanthin (E161g), cryptoxanthin (E161c), rubixanthin (E161d), violanxanthin (E161e), rhodoxanthin (E161f), caramel (E150(a-d)), β-apo-8'-carotenal (E160e), β-carotene (E160a), alpha carotene, gamma carotene, ethyl ester of beta-apo-8 carotenal (E160f), flavoxanthin (E161a), lutein (E161b), cochineal extract (E120); carmine (E132), carmoisine/azorubine (E122), sodium copper chlorophyllin (E141), chlorophyll (E140), toasted partially defatted cooked cottonseed flour, ferrous gluconate, ferrous lactate, grape color extract, grape skin extract (enocianina), anthocyanins (E163), *haematococcus* algae meal, synthetic iron oxide, iron oxides and hydroxides (E172), fruit juice, vegetable juice, dried algae meal, *tagetes* (Aztec marigold) meal and extract, carrot oil, corn endosperm oil, paprika, paprika oleoresin, phaffia yeast, riboflavin (E101), saffron, titanium dioxide, turmeric (E100), turmeric oleoresin, amaranth (E123), capsanthin/capsorbin (E160c), lycopene (E160d), or a combination comprising at least one of the foregoing.

In some embodiments, exemplary certified colors can include FD&C blue #1, FD&C blue #2, FD&C green #3, FD&C red #3, FD&C red #40, FD&C yellow #5 and FD&C yellow #6, tartrazine (E102), quinoline yellow (E104), sunset yellow (E110), ponceau (E124), erythrosine (E127), patent blue V (E131), titanium dioxide (E171), aluminium (E173), silver (E174), gold (E175), pigment rubine/lithol rubine BK (E180), calcium carbonate (E170), carbon black (E153), black PN/brilliant black BN (E151), green S/acid brilliant green BS (E142), or a combination comprising at least one of the foregoing. In some embodiments, certified colors can include FD&C aluminum lakes. These consist of the aluminum salts of FD&C dyes extended on an insoluble substrate of alumina hydrate. Additionally, in some embodiments, certified colors can be included as calcium salts.

Acceptable coloring agents are specifically water-soluble coloring agents. Suitable amounts of colorant to provide the desired visual effect can be selected by one of ordinary skill in the art without undue experimentation using guidelines provided. Exemplary amounts of coloring agents can be about 0.005 to about 15 wt %, specifically about 0.01 to about 6 wt %, and more specifically about 0.1 to about 2 wt % each based on the total weight of the composition.

Emulsifiers can be added to the beverage composition to prevent separation of the composition components by keeping ingredients dispersed. Emulsifiers can include molecules which have both a hydrophilic part and a hydrophobic part. Emulsifiers can operate at the interface between hydrophilic and hydrophobic materials of the beverage to prevent separation of the components of the composition. Suitable emulsifiers for use in the compositions include, for example, lecithin (e.g., soy lecithin); mono and di-glycerides of long chain fatty acids, specifically saturated fatty acids, and more specifically, stearic and palmitic acid mono- and diglycerides; mono and di-glycerides of acetic acid, citric acid, tartaric acid, or lactic acid; egg yolks; polysorbates (e.g., polysorbate 20, polysorbate 40, polysorbate 60, polysorbate 65, and polysorbate 80), propylene glycol esters (e.g, propylene glycol monostearate); propylene glycol esters of fatty acids; sorbitan esters (e.g., sorbitan monostearates, sorbitan tristearates, sorbitan monolaurate, sorbitan monooleate), *Acacia* (gum arabic), sucrose monoesters; polyglycerol esters; polyethoxylated glycerols; and the like, or a combination comprising at least one of the foregoing emulsifiers.

The beverage composition may contain an emulsifier in an amount of about 0.001% to about 2.00%, specifically about 0.005% to about 1.00%, more specifically about 0.01% to about 0.5%, and yet more specifically about 0.05% to about 0.1% by weight of the composition.

Certain components (sometimes referred to as hydrocolloids) that act as thickening agents which can impart added "mouth-feel" to the composition include natural and synthetic gums, for example locust bean gum, guar gum, gellan gum, xanthan gum, gum ghatti, modified gum ghatti, tragacanth gum, carrageenan, and the like; natural and modified starches, for example pregelatinized starch (corn, wheat, tapioca), pregelatinized high amylose-content starch, pregelatinized hydrolyzed starches (maltodextrins, corn syrup solids), chemically modified starches such as pregelatinized substituted starches (e.g., octenyl succinate), and the like; cellulose derivatives, for example carboxymethylcellulose, sodium carboxymethylcellulose, and the like; polydextrose; whey or whey protein concentrate; pectin; gelatin; or a combination comprising at least one of the foregoing thickening agents.

The beverage composition may contain a thickening agent in an amount of about 0.001% to about 10%, specifically about 0.005% to about 5%, more specifically about 0.01% to about 1%, and yet more specifically about 0.05% to about 0.5% by weight of the composition.

Preservatives, including antimicrobials, can be added to the beverage composition to provide freshness and to prevent the unwanted growth of bacteria, molds, fungi, or yeast. The addition of a preservative, including antioxidants, may also be used to maintain the composition's color, flavor, or texture. Any suitable preservatives for use in food and beverage products can be incorporated into the compositions. Examples of suitable preservatives include benzoic acid alkali metal salts (e.g., sodium benzoate), sorbic acid alkali metal salts (e.g., potassium sorbate), ascorbic acid (Vitamin C), citric acid, calcium propionate, sodium erythorbate, sodium nitrite, calcium sorbate, butylated hydroxyanisole (BHA), butylated hydroxytoluene (BHT), ethylenediaminetetraacetic acid (EDTA), tocopherols (Vitamin E), straight chain polyphosphates, or a combination comprising at least one of the foregoing preservatives.

The beverage composition may contain the preservative or preservative combination in an amount of about 0.0001% to about 0.10%, specifically about 0.001% to about 0.08%, more specifically about 0.005% to about 0.05%, and yet more specifically about 0.01% to about 0.04% by weight of the composition.

The beverage composition may be fortified or enriched with vitamins, minerals, micronutrients, or other nutrients. Micronutrients can include materials that have an impact on the nutritional well being of an organism even though the quantity required by the organism to have the desired effect is small relative to macronutrients such as protein, carbohydrate, and fat. Micronutrients can include, but are not limited to vitamins, minerals, enzymes, phytochemicals, antioxidants, and combinations thereof.

Suitable vitamins or vitamin precursors include ascorbic acid (Vitamin C), beta carotene, niacin (Vitamin $B_3$), riboflavin (Vitamin $B_2$), thiamin (Vitamin $B_1$), niacinamide, folate or folic acid, alpha tocopherols or esters thereof, Vitamin D, retinyl acetate, retinyl palmitate, pyridoxine (Vitamin $B_6$), folic acid (Vitamin $B_9$), cyanocobalimin (Vitamin $B_{12}$), pantothenic acid, biotin, or a combination comprising at least one of the foregoing vitamins.

In some embodiments, vitamins or vitamin precursors may include fat soluble vitamins such as vitamin A, vitamin D, vitamin E, and vitamin K and combinations thereof. In some embodiments, vitamins or vitamin precursors can include water soluble vitamins such as vitamin C (ascorbic acid), the B vitamins (thiamine or $B_1$, riboflavin or $B_2$, niacin or $B_3$, pyridoxine or $B_6$, folic acid or $B_9$, cyanocobalimin or $B_{12}$, pantothenic acid, biotin), and combinations thereof.

Exemplary minerals include sodium, magnesium, chromium, iodine, iron, manganese, calcium, copper, fluoride, potassium, phosphorous, molybdenum, selenium, zinc, or a combination comprising at least one of the foregoing minerals. The minerals can be provided as a mineral salt, including carbonate, oxide, hydroxide, chloride, sulfate, phosphate, pyrophosphate, gluconate, lactate, acetate, fumarate, citrate, malate, amino acids and the like for the cationic minerals and sodium, potassium, calcium, magnesium and the like for the anionic minerals.

The amount of vitamins or minerals provided in the compositions may be up to or exceeding amounts generally recognized as U.S. Recommended Daily amounts or the Recommended Daily Intake amounts established by the U.S. Food and Drug Administration.

In some embodiments micronutrients may include but are not limited to L-carnitine, choline, coenzyme Q10, alpha-lipoic acid, omega-3-fatty acids, pepsin, phytase, trypsin, lipases, proteases, cellulases, and combinations thereof.

Antioxidants may include materials that scavenge free radicals. In some embodiments, antioxidants can include but are not limited to ascorbic acid, citric acid, rosemary oil, vitamin A, vitamin E, vitamin E phosphate, tocopherols, di-alpha-tocopheryl phosphate, tocotrienols, alpha lipoic acid, dihydrolipoic acid, xanthophylls, beta cryptoxanthin, lycopene, lutein, zeaxanthin, astaxanthin, beta-carotene, carotenes, mixed carotenoids, polyphenols, flavonoids, and combinations thereof.

Exemplary nutrients also may include amino acids such as L-tryptophan, L-lysine, L-leucine, L-methionine, 2-aminoethanesulfonic acid (taurine), and L-carnitine; creatine; glucuronolactone; inositol; or a combination comprising at least one of the foregoing nutrients.

Phytochemicals ("phytonutrients") are plant derived compounds which may provide a beneficial effect on the health or well-being of the consumer. Phytochemicals include plant derived antioxidants, phenolic compounds including monophenols and polyphenols, and the like. Exemplary phytochemicals include lutein, lycopene, carotene, anthocyanin, capsaicinoids, flavonoids, hydroxycinnamic acids, isoflavones, isothiocyanates, monoterpenes, chalcones, coumestans, dihydroflavonols, flavanoids, flavanols, quercetin, flavanones, flavones, flavan-3-ols (catechins, epicatechin, epigallocatechin, epigallocatechingallate, and the like), flavonals (anthocyanins, cyanidine, and the like); phenolic acids; phytosterols, saponins, terpenes (carotenoids), or a combination comprising at least one of the foregoing phytochemicals.

The phytochemicals may be provided in substantially pure or isolated form or in the form of natural plant extracts. Suitable plant extracts which contain one or more phytochemicals include fruit skin extracts (grape, apple, crab apple, and the like), green tea extracts, white tea extracts, green coffee extract, or a combination comprising at least one of the foregoing extracts.

Various herbals, aromatic plants or plant parts or extracts thereof, also may be included in the compositions for a variety of reasons such as for flavor or for their potential health benefits. Exemplary herbals include Echinacea, Goldenseal, *Calendula*, Rosemary, Thyme, Kava Kava, Aloe, Blood Root, Grapefruit Seed Extract, Black Cohosh, Ginseng, Guarana, Cranberry, *Ginko Biloba*, St. John's Wort, Evening Primrose Oil, Yohimbe Bark, Green Tea, Ma Huang, Maca, Bilberry, extracts thereof, or a combination comprising at least one of the foregoing herbals.

Concentrate Compositions

Concentrate compositions may be in dry form (e.g., powder or tablet) or in liquid form (e.g., syrup, suspension, or emulsion). Concentrate compositions typically include the flavoring agent in a volume of liquid medium that is less than the volume of liquid medium found in the finished beverage. Other optional components in the concentrate include sweetening agents, coloring agents, and other additives such as food-grade acids, preservatives, and the like. The bulk of the liquid component of a finished beverage composition is not present in the concentrate to allow for reduced weight, volume, storage and shipping costs while at the same time allowing for increased shelf life of the concentrate versus beverage composition.

In one embodiment, the concentrate composition is formulated to provide final beverage compositions upon dilution with about a 2-fold to about a 5-fold by volume, specifically about 3-fold to about a 4-fold by volume of a liquid. The liquid may be water, juice, dairy component, a non-dairy milk, ethanol, a combination comprising at least one of the foregoing, and the like. The liquid may be in noncarbonated or carbonated form.

Methods and Kits for Remineralization

Some embodiments described herein extend to methods of remineralizing tooth enamel of a mammal, particularly remineralizing enamel subsurface lesions. Such methods may be particularly useful for remineralizing tooth enamel of humans. In accordance with such methods, any of the oral delivery systems described above may be applied into the oral cavity of a mammal. The product may include a phosphopeptide or phosphoprotein stabilized calcium phosphate or calcium fluoride phosphate complex, such as CPP-ACP, and a calcium and/or phosphate salt, as described herein. Any of the other optional additives described above also may be included.

Once the oral delivery system is applied into the oral cavity, it may be retained therein for a time sufficient to remineralize tooth enamel. Such time periods may be at least 1 minute, more specifically, at least 10 minutes in some embodiments. These methods remineralize tooth enamel by an amount greater than consuming an oral delivery system that is substantially the same but free of the complex and the salt over the same period of time.

More specifically, in some embodiments, consuming one of the sugared confectionery or chewing gum products described above may remineralize tooth enamel by at least about 2.8% more, and in some embodiments at least about 8% more, than consuming sugared confections or chewing gums which are substantially the same but free of CPP-ACP and the calcium and/or phosphate salt. In some embodiments including CPP-ACP, calcium lactate and phosphate salts, for example, consuming one of these sugared confectionery or chewing gum products may remineralize tooth enamel by about 7% more, and in some embodiments at least about 12.5% more, than consuming sugared confections or chewing gums which are substantially the same but free of CPP-ACP, calcium lactate and phosphate salts.

Some embodiments described herein may extend to kits for addressing the problem of demineralization of tooth enamel in mammals. In particular, in some embodiments, a kit may be provided for remineralizing tooth enamel, particularly enamel subsurface lesions in the tooth of a mammal. The kit may include any of the oral delivery systems described above, which may include a phosphopeptide or phosphoprotein stabilized calcium phosphate or calcium fluoride phosphate complex and a calcium and/or phosphate salt. The kit also may include a set of instructions for using the oral delivery system and a package for housing the oral delivery system and the set of instructions.

The features and advantages of the present invention are more fully shown by the following examples which are provided for purposes of illustration, and are not to be construed as limiting the invention in any way.

EXAMPLES

Example 1

This example shows the remineralization effects of sugared confectionery products containing CPP-ACP as compared to that of control sugared confectionery products and control sugar-free confectionery products.

Two different sugared hard candies containing CPP-ACP were prepared according to the formulations in Table 1 below. The first sugared hard candy ("A") contained 0.5% CPP-ACP and the second sugared hard candy ("B") contained 1% CPP-ACP. A control sugared hard candy, which was free of CPP-ACP, was prepared according to the formulation in Table 1 below. A control sugar-free hard candy, which was free of CPP-ACP, also was prepared according to the formulation in Table 1 below.

TABLE 1

Hard candy formulations

| | Weight % | | | |
|---|---|---|---|---|
| Component | A | B | Sugared Control | Sugar-Free Control |
| Sugar, fine granulated | 61.8261 | 61.5011 | 62.1511 | — |
| Corn syrup | 33.2909 | 33.1159 | 33.4659 | — |
| Apple juice concentrated | 0.1360 | 0.1360 | 0.1360 | 0.1360 |
| Green color (FD&C Blue) | 0.0010 | 0.0010 | 0.0010 | 0.0010 |
| Citric acid | 0.5460 | 0.5460 | 0.5460 | 0.5460 |
| Malic acid | 0.3000 | 0.3000 | 0.3000 | 0.3000 |
| Sugar-free hard candy salvage | 3.0000 | 3.0000 | 3.0000 | 3.0000 |
| Apple flavor | 0.4000 | 0.4000 | 0.4000 | 0.4000 |
| CPP-ACP | 0.5000 | 1.0000 | — | — |
| Isomalt | — | — | — | 95.4170 |
| Acesulfame-K | — | — | — | 0.2000 |

Individual sugared hard candies were formulated according to Table 1 above. The sugared candy of formulation A contained 19.3 mg of CPP-ACP. The sugared candy of formulation B contained 38.5 mg of CPP-ACP. The sugared control candy was identical to the sugared candies A and B except formulated without the CPP-ACP. The sugar-free control candy was identical to the sugared candies A and B except formulated without the CPP-ACP and with sugarless sweeteners instead of the sugar sweeteners.

The sugared hard candies containing CPP-ACP and the control hard candies were used in a double-blind, randomized cross-over trial designed to measure the comparative remineralization of tooth enamel. The trial was conducted using 10 adult subjects who wore removable palatal appliances with four human-enamel half-slabs containing subsurface demineralized lesions. The appliances were worn for the following times: 8:00 am to 10:30 am, 11:00 am to 1:00 pm, 2:00 pm to 3:00 pm, 3:30 pm to 6:00 pm, 8:00 pm to 9:00 pm and 10:00 pm to 7:00 am. The hard candies were consumed seven times per day for a seven day period at the following times: 8:00 am, 9:00 am, 11:00 am, 12:00 pm, 2:00 pm, 4:00 pm and 8:00 pm. The subjects then crossed over to each of the other candies with a one-week washout period between candy formulations.

After each treatment period, the enamel slabs were removed, paired with their respective demineralized controls and subjected to microradiography and computer-assisted densitometric image analysis to determine the level of remineralization. The sugared hard candies containing CPP-ACP promoted remineralization of tooth enamel by a greater amount than the control sugared hard candy.

In particular, the control sugared hard candy produced 6.1%±0.8% demineralization of the enamel subsurface lesions. The sugared hard candy of formulation A (0.5% CPP-ACP) produced 3.5%±0.7% enamel subsurface remineralization. The sugared hard candy of formulation B (1% CPP-ACP) produced 8.6%±0.6% enamel subsurface remineralization. These results, which also are depicted in FIG. 1, showed that the incorporation of CPP-ACP into sugared hard candies not only prevented demineralization, but also significantly promoted remineralization of enamel subsurface lesions in the tooth.

Further, the sugared hard candy of formulation B (containing 1% CPP-ACP) promoted remineralization of tooth enamel by a greater amount than the control sugar-free hard candy. In general, sugar-free confections do not include sugars, and thus, do not lead to the production of organic acids that cause demineralization of the tooth enamel, as in sugared confections. Additionally, sugar-free confections allow the tooth enamel to undergo typical remineralization processes through production of saliva during consumption of the confection. The control sugar-free hard candy of this Example, therefore, promoted remineralization through a different mechanism than the sugared hard candies of formulations A and B. In particular, the control sugar-free hard candy produced 4.8%±0.9% enamel subsurface remineralization. As discussed above, the sugared hard candy of formulation B (containing 1% CPP-ACP) produced 8.6%±0.6% enamel subsurface remineralization. This difference in remineralization was statistically significant, i.e., the sugared hard candy of formulation B promoted remineralization of tooth enamel significantly more than the control sugar-free hard candy. These results also are depicted in FIG. 1.

Therefore, sugared confectionery products containing CPP-ACP significantly promoted remineralization of tooth enamel.

Example 2

This example shows the remineralization effects of sugared confectionery products containing CPP-ACP, calcium lactate and sodium phosphates as compared to that of control sugared confectionery products and control sugar-free confectionery products.

Two different sugared hard candies containing CPP-ACP, calcium lactate and sodium phosphates were prepared according to the formulations in Table 3 below. The first sugared hard candy ("C") contained 0.1% CPP-ACP, 1.6% calcium lactate and 1.5% sodium phosphates, and the second sugared hard candy ("D") contained 0.1% CPP-ACP, 2.8% calcium lactate and 1.7% sodium phosphates. A control sugared hard candy, which was free of CPP-ACP, calcium lactate and sodium phosphates, was prepared according to the formulation in Table 3 below. A control sugar-free hard candy, which was free of CPP-ACP, calcium lactate and sodium phosphates, also was prepared according to the formulation in Table 3 below.

TABLE 3

Hard candy formulations

| Component | Weight % | | | |
|---|---|---|---|---|
| | C | D | Sugared Control | Sugar-Free Control |
| Sugar, fine granulated | 46.1498 | 50.3093 | 52.8998 | — |
| Corn syrup | 47.0355 | 41.1704 | 43.2693 | — |
| Calcium lactate pentahydrate | 1.4498 | 2.8284 | — | — |
| Sodium phosphate dibasic | 0.9064 | 1.0098 | — | — |
| Citric acid | 0.9060 | 1.0094 | 0.9829 | 0.6848 |
| Sodium phosphate monobasic anhydrous | 0.6411 | 0.7143 | — | — |
| Tangerine oil | 0.1737 | 0.1935 | 0.1884 | 0.1313 |
| Orange oil | 0.1471 | 0.1638 | 0.1595 | 0.1111 |
| CPP-ACP | 0.0906 | 0.1009 | — | — |
| Residual moisture | 2.5000 | 2.5000 | 2.5000 | 2.5000 |
| Potable water | — | — | — | 23.0740 |
| Isomalt | — | — | — | 73.4989 |

Individual sugared hard candies were formulated according to Table 3 above. The sugared control candy was identical to the sugared candies C and D except formulated without the CPP-ACP, calcium lactate and sodium phosphates. The sugar-free control candy was identical to the sugared candies C and D except formulated without the CPP-ACP, calcium lactate and sodium phosphates and with sugarless sweetener instead of the sugar sweeteners.

The sugared hard candies containing CPP-ACP, calcium lactate and sodium phosphates and the control hard candies were used in a double-blind, randomized cross-over trial designed to measure the comparative remineralization of tooth enamel. The trial was conducted using 12 adult subjects who wore removable palatal appliances with four human-enamel half-slabs containing subsurface demineralized lesions. The appliances also contained two slabs of sound enamel. The appliances were worn for the following times: 8:00 am to 10:30 am, 11:00 am to 1:00 pm, 2:00 pm to 3:00 pm, 3:30 pm to 6:00 pm, 8:00 pm to 9:00 pm and 10:00 pm to 7:00 am. The hard candies were consumed seven times per day for a seven day period at the following times: 8:00 am, 9:00 am, 11:00 am, 12:00 pm, 2:00 pm, 4:00 pm and 8:00 pm. The subjects then crossed over to each of the other candies with a one-week washout period between candy formulations.

After each treatment period, the enamel slabs were removed, paired with their respective demineralized controls and subjected to microradiography and computer-assisted densitometric image analysis to determine the level of remineralization. The sugared hard candies containing CPP-ACP, calcium lactate and sodium phosphates promoted remineralization of tooth enamel by a greater amount than the control sugared hard candy.

Figure 2:
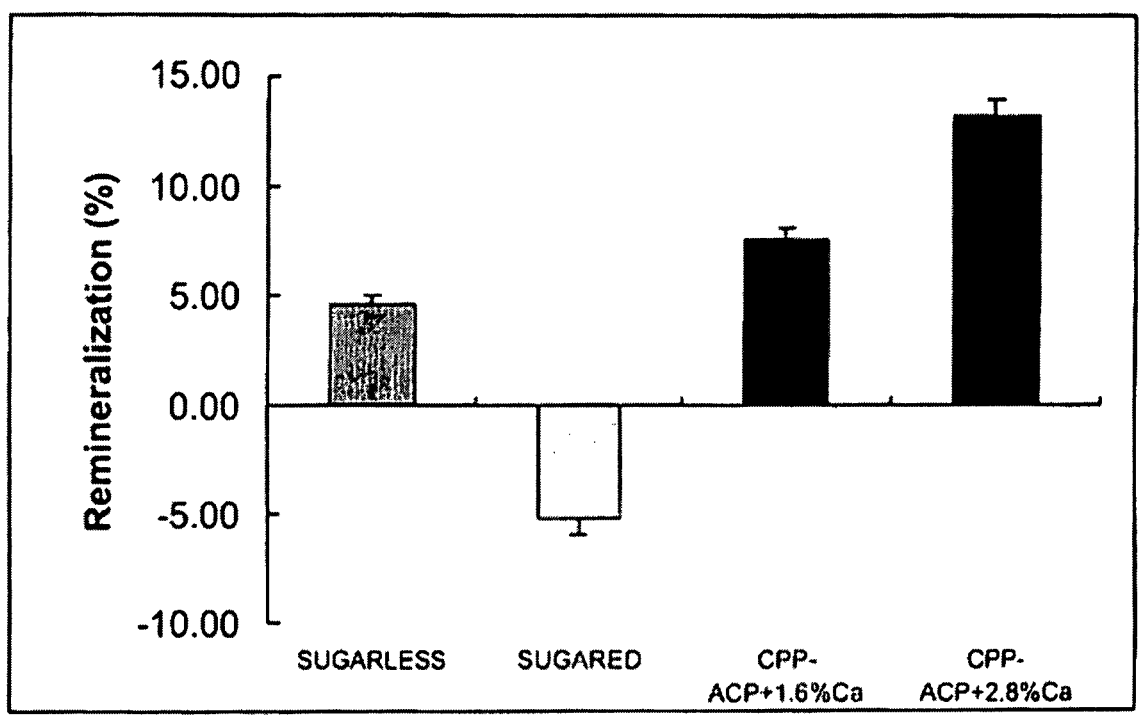
FIG. 2 is a graphical representation of the percentage of remineralization of enamel subsurface lesions provided by two sugared confectionery compositions including CPP-ACP, calcium lactate and phosphate salts according to the present invention as compared to a sugared control and a sugar-free control.

In particular, the control sugared hard candy produced 5.23%±0.71% demineralization of the enamel subsurface lesions. The sugared hard candy of formulation C (0.1% CPP-ACP, 1.6% calcium lactate and 1.5% sodium phosphates) produced 7.49%±0.60% enamel subsurface remineralization. The sugared hard candy of formulation D (0.1% CPP-ACP, 2.8% calcium lactate and 1.7% sodium phosphates) produced 13.20%±0.74% enamel subsurface remineralization. These results, which also are depicted in FIG. 2, showed that the incorporation of CPP-ACP, calcium lactate and sodium phosphates into sugared hard candies not only prevented demineralization, but also significantly promoted remineralization of enamel subsurface lesions in the tooth.

The sugared hard candies containing CPP-ACP, calcium lactate and sodium phosphates also promoted remineralization of tooth enamel by a greater amount than the control sugar-free hard candy. As discussed above, sugar-free confections remineralize tooth enamel by allowing typical remineralization processes to proceed. The control sugar-free hard candy of this Example, therefore, promoted remineralization through a different mechanism than the sugared hard candies of formulations C and D. In particular, the control sugar-free hard candy produced 4.53%±0.51% enamel subsurface remineralization. As provided above, the sugared hard candy of formulation C (0.1% CPP-ACP, 1.6% calcium lactate and 1.5% sodium phosphates) produced 7.49%±0.60% enamel subsurface remineralization. The sugared hard candy of formulation D (0.1% CPP-ACP, 2.8% calcium lactate and 1.7% sodium phosphates) produced 13.20%±0.74% enamel subsurface remineralization. In view thereof, the incorporation of CPP-ACP, calcium lactate and sodium phosphates into sugared hard candies also significantly promoted remineralization of enamel subsurface lesions in the tooth as compared to sugar-free hard candies. These results also are depicted in FIG. 2.

The sound enamel results were similar to the results for the enamel subsurface lesions. In particular, the control sugared hard candy produced 4.03±1.11% demineralization of sound enamel. The control sugar-free hard candy produced 0.68±0.70% mineralization of sound enamel. The sugared hard candy of formulation C (0.1% CPP-ACP, 1.6% calcium lactate and 1.5% sodium phosphates) produced 0.85%±0.51% mineralization of sound enamel. The sugared hard candy of formulation D (0.1% CPP-ACP, 2.8% calcium lactate and 1.7% sodium phosphates) produced 1.2%±0.73% mineralization of sound enamel. These results showed that the incorporation of CPP-ACP, calcium lactate and sodium phosphates into sugared hard candies prevented demineralization of sound enamel.

Example 3

TABLE 4

Remineralizing Film

| Component | % by weight (wet basis) |
|---|---|
| Sweetener blend (xylitol, Ace-sulfame K, sucralose) | 2.82 |
| Water | 65.12 |
| Color solution (FD&C Yellow #6) | 2.00 |
| Hydrocolloid blend (sodium alginate, pectin, modified starch) | 17.47 |
| Flavor | 7.76 |
| CPP-ACP | 0.10 |
| Calcium lactate | 1.5 |
| Plasticizer (glycerin) | 3.23 |

An edible remineralizing film is prepared according to the formulation in Table 4 above.

The film is prepared by first dissolving the sweeteners (xylitol, Ace-sulfame K and sucralose) and color in water. The hydrocolloids are added and dispersed in the solution. A high shear mixer is used, as necessary, to remove lumps. The hydrocolloids are allowed to hydrate for one and a half hours, after which the plasticizer (glycerine), CPP-ACP, calcium lactate and flavor are added. The batch is mixed and allowed to rest for fifteen to thirty minutes.

Subsequently, the film is cast on a hot plate at 74° C. In particular, a water bath is placed on the hot plate, and the film is cast onto a stainless steel plate that is placed above the water bath. If the temperature of the hot plate becomes too high, i.e., boiling water, the film fuses to the plate causing difficulties in removal. Once dried, the film is peeled from the plate and after equilibration (about twenty-four hours) strips are cut.

Example 4

TABLE 5

Iced Tea Beverage

| Component | Amount % w/v |
|---|---|
| Sucrose | 7.000 |
| Citric acid | 0.200 |
| Tea extract "Assam" | 0.120 |
| Lemon Juice Concentrate | 0.100 |
| Sodium benzoate (20% solution) | 0.075 |
| CPP-ACP | 0.050 |
| Calcium lactate | 0.050 |
| Sodium phosphates | 0.050 |
| Water | to volume |

A beverage composition is prepared according to the formulation in Table 5 above.

All components except sodium benzoate are weighed and added into a volumetric flask using a funnel. The flask is filled with water almost to the fill line and then the sodium benzoate is added. The flask is filled with water to the fill line and inverted. If necessary, the flask is placed on a magnetic stirrer until all components are fully dissolved.

Example 5

TABLE 6

Dentifrice Composition

| Component | Wt. % |
|---|---|
| Sorbitol | 24.0 |
| Glycerine | 14.45 |
| Polyethylene glycol (PEG) 600 | 4.0 |
| Carboxymethyl cellulose | 0.5 |
| Sodium saccharin | 0.4 |
| Sodium fluoride | 0.25 |
| Deionized water | 27.0 |
| Titanium dioxide | 0.4 |
| Sodium benzoate | 0.4 |
| Flavorants | 1.0 |
| Sodium tripolyphosphate | 5.0 |
| Silica microparticles | 19.1 |
| CPP-ACP | 0.1 |

TABLE 6-continued

Dentifrice Composition

| Component | Wt. % |
|---|---|
| Calcium lactate | 1.5 |
| Sodium phosphates | 1.5 |
| Colorant | 0.4 |

A dentifrice composition is prepared according to the formulation in Table 6 above.

The jacket temperature of a mixing tank is set to about 150° F. (65° C.). The humectants (glycerine, sorbitol, PEG) and water are added to the mixing tank and agitation is started. When the temperature reaches about 120° F. (50° C.), sweetening agents (saccharin), fluoride, chelant (sodium tripolyphosphate), coloring agents (titanium dioxide) and sodium benzoate are added. Thickening agents (carboxymethyl cellulose) are added to the silica abrasive and the resulting mixture is added to the mixing tank with high agitation. The CPP-ACP, calcium lactate and sodium phosphates are added to the combination and mixing is continued. The tank is cooled to 120° F. (50° C.) and the flavoring agents are added. Mixing is continued for approximately 5 minutes to yield the final composition.

The invention claimed is:

1. An oral delivery system comprising:
    (a) a casein phosphopeptide-calcium phosphate complex; and
    (b) a calcium salt and a phosphate salt, wherein each of said salts is a separate and additional component from said complex, and wherein said calcium salt is selected from the group consisting of calcium chloride, calcium lactate, calcium sulfate, calcium carbonates, calcium phosphates, calcium glutareate, calcium malate, calcium citrate, calcium gluconate, calcium glycerophosphate, calcium fumarate, calcium hydroxide, calcium oxide and combinations thereof, and said phosphate salt is selected from the group consisting of neutral, monobasic and dibasic sodium phosphate salts; and
    wherein said oral delivery system is a sugar-containing chewing gum or confectionery;
    wherein said casein phosphopeptide calcium phosphate complex is present in an amount that is less by weight than that of said salts, and said casein phosphopeptide calcium phosphate complex is present in an amount of from about 0.1% to about 0.5% by weight of said system, said calcium salt is present in an amount of from about 1.5% to about 3.0% by weight of said system, and said phosphate salt is present in an amount of from 1.2% to about 1.8% by weight of said system; and
    wherein upon consumption said system provides a level of enamel subsurface remineralization in the tooth of a mammal that is at least about 12.5% greater than the amount of remineralization provided by consumption of a composition which is substantially the same as said system but which is free of said complex and said salts.

2. The oral delivery system of claim 1, wherein said calcium salt is calcium lactate.

3. The oral delivery system of claim 1, wherein said system is a chewing gum.

4. The oral delivery system of claim 1, wherein said system is free of added sodium bicarbonate.

* * * * *